United States Patent [19]
Walker

[11] Patent Number: 5,855,817
[45] Date of Patent: Jan. 5, 1999

[54] WATERPROOFING AND PRESERVATIVE COMPOSITIONS AND PREPARATION THEREOF

[75] Inventor: Leigh E. Walker, Macungie, Pa.

[73] Assignee: Lonza, Inc., Annandale, N.J.

[21] Appl. No.: 890,130

[22] Filed: Jul. 9, 1997

Related U.S. Application Data

[63] Continuation of Ser. No. 74,314, Jun. 9, 1993.

[51] Int. Cl.$^6$ .............. C09K 15/32; C09K 5/14; B05D 3/00; C09D 5/16

[52] U.S. Cl. ............ 252/400.41; 422/1; 427/297; 427/393; 427/393.4; 427/397; 427/440; 428/541; 106/2; 106/15.05; 106/18.32

[58] Field of Search ................ 422/1; 106/2, 15.05, 106/18.32; 428/541; 252/380, 194, 403, 400.41; 427/297, 393, 393.4, 397, 440

[56] References Cited

U.S. PATENT DOCUMENTS

| | | | |
|---|---|---|---|
| 2,737,458 | 3/1956 | Burnham | 106/171 |
| 2,994,699 | 8/1961 | De Benneville | 546/237 |
| 3,169,983 | 2/1965 | Hunter | 558/291 |
| 3,233,645 | 2/1966 | Kalberg | 411/110 |
| 3,281,458 | 10/1966 | Jordan et al. | 562/400 |
| 3,301,815 | 1/1967 | Hunyar et al. | 524/189 |
| 3,406,038 | 10/1968 | Moren | 427/342 |
| 3,600,408 | 8/1971 | Bursack | 106/2 |
| 3,646,147 | 2/1972 | Dadekian | 564/481 X |
| 3,661,633 | 5/1972 | Moren | 428/541 |
| 3,666,690 | 5/1972 | Bann | 252/547 |
| 4,134,771 | 1/1979 | Bentsen | 106/15.05 |
| 4,143,010 | 3/1979 | Rak | 514/433 |
| 4,276,329 | 6/1981 | Vasishth et al. | 427/393 |
| 4,313,977 | 2/1982 | Johnson et al. | 427/342 |
| 4,360,385 | 11/1982 | Grunewalder | 106/2 |
| 4,404,239 | 9/1983 | Grunewalder | 106/2 |
| 4,496,613 | 1/1985 | Zagefka et al. | 427/440 |
| 4,500,338 | 2/1985 | Young et al. | 504/151 |
| 4,508,568 | 4/1985 | Fox | 106/2 |
| 4,585,795 | 4/1986 | Linderborg | 514/558 |
| 4,716,060 | 12/1987 | Rajadhyaksha et al. | 106/18.32 |
| 4,749,411 | 6/1988 | Chapin | 106/18.32 |
| 4,877,654 | 10/1989 | Wilson | 427/387 |
| 4,911,858 | 3/1990 | Bunczk et al. | 252/106 |
| 4,923,894 | 5/1990 | Kanda et al. | 514/493 |

(List continued on next page.)

FOREIGN PATENT DOCUMENTS

| | | |
|---|---|---|
| 2078412 | 3/1993 | Canada . |
| 2078413 | 3/1993 | Canada . |
| 618433 | 2/1949 | United Kingdom . |
| 650304 | 2/1951 | United Kingdom . |
| 669506 | 4/1952 | United Kingdom . |
| 719617 | 12/1954 | United Kingdom . |
| 795814 | 5/1958 | United Kingdom . |

OTHER PUBLICATIONS

"Toxin" Drugs, Pollut, Mae. Anim. Bolis et al. Jan. 1984 pp. 26–42, as abstracted by Chemical Abstract 102:108236.

JP 0201105 (Jan. 1990) as abstracted by Chem. Ab. 112:223132.

JP 03197415 (Aug. 1991) as abstracted by Chem Ab. 116:27826.

De 2824716 (Dec. 1979) as abstracted by Chem Ab. 93:9690.

Pogrebinskaya, E.A. "Effect of Antistatic Finishing of Knitted Acrylic Textiles on their Soiling" Nauch.–Issled. Tr., Vses. Nauch.–Issled . . . Prom., No. 11, Jan. 1972, pp. 33–39 as Abstracted by Chem. Ab. 81:38736.

(List continued on next page.)

Primary Examiner—C. H. Kelly
Attorney, Agent, or Firm—Darby & Darby

[57] ABSTRACT

Polyhydroxyl and polyether hydroxyl esters of fatty acids and polyether hydroxides are provided as waterproofers. These waterproofers are also combined with quaternary ammonium compositions and a solvent in waterproofing, wood preservative systems. Preferred quaternary ammonium compounds have chloride, hydroxide, carbonate, carboxylate, or borate counter ions.

88 Claims, 2 Drawing Sheets

U.S. PATENT DOCUMENTS

| | | | |
|---|---|---|---|
| 4,929,454 | 5/1990 | Findlay | 424/638 |
| 4,950,685 | 8/1990 | Ward | 514/479 |
| 4,970,201 | 11/1990 | Giebler et al. | 514/64 |
| 4,992,307 | 2/1991 | Ikeda | 427/297 |
| 5,004,760 | 4/1991 | Patton et al. | 424/78.27 |
| 5,049,383 | 9/1991 | Huth et al. | 424/405 |
| 5,077,098 | 12/1991 | Chow | 427/397 |
| 5,080,935 | 1/1992 | Kelso, Jr. et al. | 427/351 |
| 5,089,483 | 2/1992 | Tsuda et al. | 514/64 |
| 5,112,396 | 5/1992 | Hegarty | 106/15.05 |
| 5,169,624 | 12/1992 | Ziegler et al. | 424/59 |
| 5,256,422 | 10/1993 | Albert et al. | 424/450 |
| 5,304,237 | 4/1994 | Barth et al. | 106/18.3 |
| 5,344,482 | 9/1994 | Landsiedel et al. | 106/18.33 |
| 5,395,656 | 3/1995 | Liang | 427/393 |
| 5,399,762 | 3/1995 | Walker | 564/296 |
| 5,409,527 | 4/1995 | Baker et al. | 106/2 |
| 5,438,034 | 8/1995 | Walker | 501/55 |

OTHER PUBLICATIONS

JP 03261711 (Nov. 1991) as abstracted by Chemical Abstract 116:136009.

EP 485251 (May 1992) as abstracted by Chem. Abstract. 117:137407.

DE 4405510 (Aug. 1995) as abstracted by Chem. Ab. 123:237499.

L. Jin & K. Archer, "Cooper Based Wood Preservatives: Observation on Fixation, Distribution and Performance" preprints for *American Wood–Preservers' Association* April 1991 meeting.

D.D. Nicholas et al., "Distribution and Permanency of DDAC in Southern Pine Sapwood Treated by the Full–Cell Process", *Forest Products Journal* 41 (1):41–45 (Jan. 1991).

L. Jin & A.F. Preston, "The Interaction of Wood Preservatives With Lignocellulosic Substrates" *Holzforschung* 45 (6):455–459 (1983).

*Proc. Amer. Wood–Preservers Assoc.* 80:191–209 (1984).

Y. Nakama, F. Harusawa & I. Murotani, "Cloud Point Phenomena In Mixtures of Anionic and Cationic Surfactants in Aqueous Solution" *JAOCS* 67 (11):717–721, (Nov. 1990).

A.F. Preston et al., "Recent Research on Alkylammonium Compounds In The U.S.", *American Wood–Preserversp3 Association*, 83:331–348 (1987).

"Quaternary Ammonium Compounds, Fine & Functional Chemicals" *AKZO*, pp. 1, 3–20 (1980).

D.D. Miller et al., "Control of Aggregate Structure With Mixed Counterions In An Ionic Double–Chained Surfactant", *Langmuir* 4(6):1363–1367 (1988).

Ewa Z. Radlinska et al., "Supra–Self Assembly: Vesicle–Micelle Equilibrium", *Colloids and Surfaces* 46:213–217 (1990).

J.E. Brady et alf., "Counterion Specificity As The Determinant of Surfactant Aggregation" *J. Phys. Chem.* 90:1853–1859, (1986).

D.D. Miller et al., "Fluorescence Quenching In Double–Chained Surfactants. 1. Theory of Quenching In Micelles and Vesicles" *J. Phys. Chem.* 93:323–325 (1989).

J.E. Brady et al., "Spontaneous Vesicles", *J. American Chemical Society* 106:4279–4280 (1984).

A.F. Preston, "Dialkyldimethylammonium Halides As Wood Preservatives", *JAOCS* 60 (3):567–570 (Mar. 1983).

D. D. Nicholas & A.F. Preston, "Interaction of Preservatives With Wood" *Chemistry of Solid Wood*, pp. 307–320 (1984).

E.W. Anacker and H.M. Ghose, "Counterions and Micelle Size I. Light Scattering by Solutions of Dodecyltrimethylammonium Salts", vol. 67 pp. 1713–1715, (Aug. 1963).

L. Sepulveda et al., "A New and Rapid Method for Preparing Long–Chain Alkyltrimethyl–ammonium Salts With A Variety of Counterions", *Journal of Colloid and Interface Science* 117 (2):460–463 (Jun. 1987).

E. Jugerman et al., *Cationic Surfactants*, pp. 56–57, Marcel Dekker Inc. (1969).

"Quaternary Ammonium Compounds", K.O. 19:521–531 (1982).

"Quaternary Ammonium Compounds", K.O. 16:859–565 (1968).

Astle,"Industrial Organic Nitrogen Compounds", Reinhold Publ. pp. 64–67 (1961).

"Organic Reactions" 11, Chaptr. 5, Krieger Publ. Co., pp. 376–383 (1960).

Carl Kaiser et al., "Alkenes via Hofmann Elimination: Use ofIon–Exchange Resin For Preparation Of Quaternary Ammonium Hydroxides: Diphenylmethyl Vinyl Ether", *Organic Synthesis*, Collective vol. VI, pp. 552–554, John Wiley, Inc. (1988).

Y. Talmon et al., "Spontaneous Vesicle Formed From Hydroxide Surfactants: Evidence Freom Electron Microscopy" *Science* 221:1047–1048 (Sep. 9, 1983).

Awata et al., "Cathodic Esterification of Carboxylic Acids", *Chemistry Letters*, pp. 371–374 (1985).

A. W. Ralston et al., "The Solubilities of Long–Chain Dialkyldimethyl–Ammonium Chlorides In Organic Solvents", Contribution from the Research Laboratory of Armour and Company 13:186–190 (1948).

A.W. Ralston et al., "Conductivities of Quaternary Ammonium Chlorides Containing Two Long–Chain Alkyl Groups", Contribution from the Research Laboratory of Armour and Company 70:977–979 (Mar. 1948).

*Organic Chemistry* 35:3597–3598 (1941).

T.P. Schultz et al., "Role of Stilbenes in the Natural Durability of Wood: Fungicidal Structure–Activity Relationships", *PhytoChemistry* 29:1501–1507 (1990).

85:123253x "A Simple Preparation of Anhydrous Tetraalkylammonium Salts" (Abstract).

115: 87485b "Wood Preservatives Containing Quaternary Ammonium Salts With Polymers" (Abstract).

112: 212470j "Agrochemical Fungicides Containing Quaternary Ammonium Salts" (Abstract).

113: 153776j "Microbicidal Thermoplastic Resin Compositions" (Abstract).

112: 79768u "Noncorrosive Quaternary Ammonium Compounds As Wood Preservatives" (Abstract).

113: 163999y "Capacitor Driving Electrolytes and Their Preparation"0 (Abstract).

112: 54969x "Preparation of Quaternary Ammonium Hydroxides Free of Halogens" (Abstract).

110: 212114e Process For Producing Quaternary Salts (Abstract).

114: 246824j "Preparation of Carbonic Half–Esters of Betaine Structure" (Abstract).

98: 200032 x "Didecyldimethylammonium Chloride — A Quaternary Ammonium Wood Preservative" (Abstract).

91: 152627b "Efficacy of Acidic and Alkaline Solutions of Alkylammonium Compounds As Wood Preservatives" (Abstract).

113: 154360f Microbicidal Coating Compositions Containing Quaternary Ammonium Salts (Abstract).

109: 124403x "Quaternary Ammonium Salt–Containing Wood Preservatives" (Abstract).
103: 109954k "Clear Aqueous Disinfectant Solutions Containing Chlorhexidine Lactate Or Gluconate And Quaternary Ammonium Salts" (Abstract).
70: 111034d "Quaternary Ammonium Bases Compatible With Scintillation–Counting Liquids" (Abstract).
60: 16447d "Nematocidal Quaternary Ammonium Salts" (abstract).
91: 109311g "Composition For Removing Water From Surfaces Of Articles" (Abstract).
75:119170u "Corrosion–Resistant Lubricants and Antistatic Agents" (Abstract).
66: 66227y "Stabilization of Vinyl Resins With Organic Quaternary Ammonium Nitrates" (Abstract).
66:1953n "N–Alkyl Ammonium Humates" (Abstract).
97: 91725.

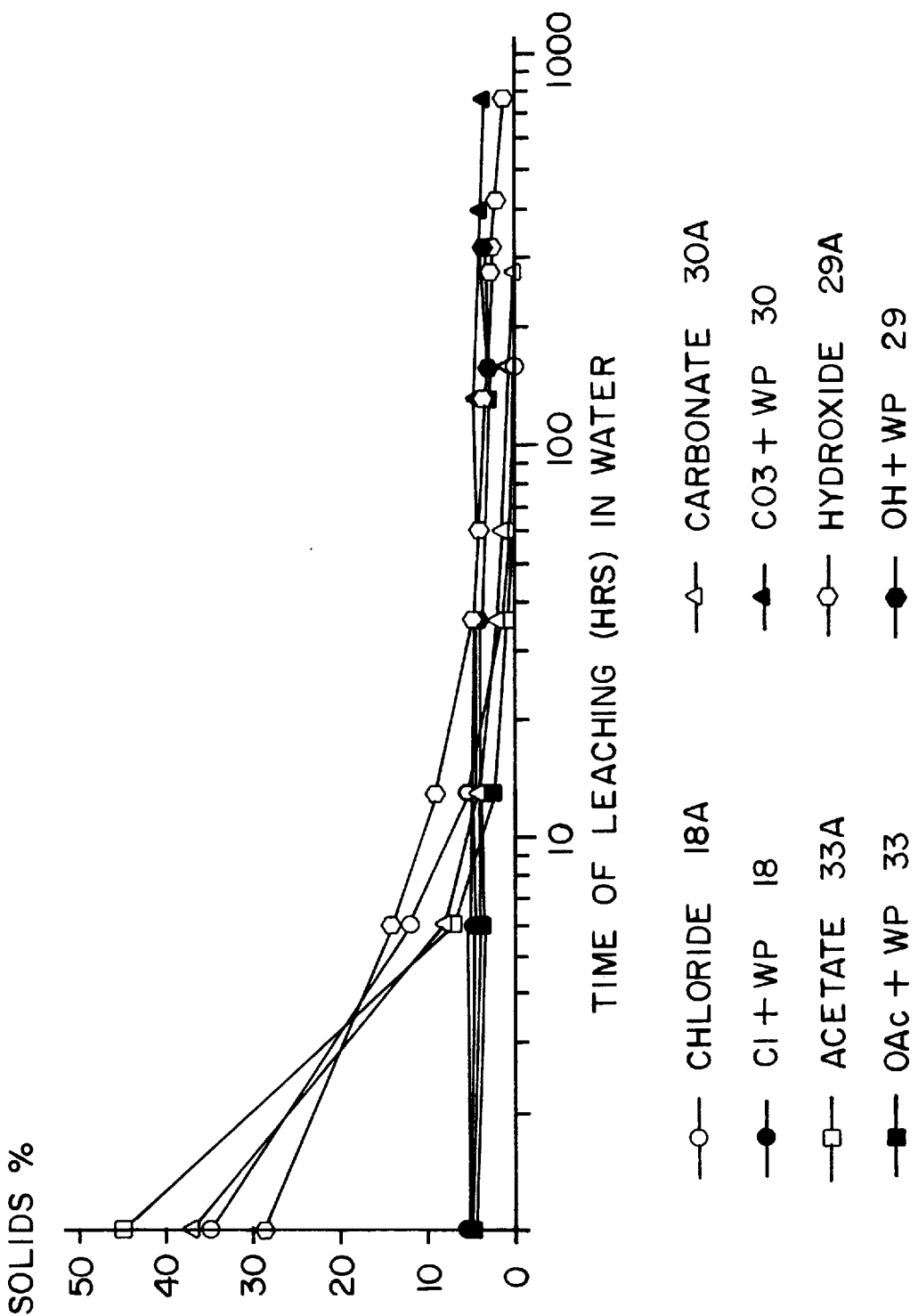

WATERPROOFING AND PRESERVATIVE COMPOSITIONS AND PREPARATION THEREOF

This is a continuation of application Ser. No. 08/074,314, filed Jun. 9, 1993.

Table of Related Applications

| Attorney's Docket No. | Appln. No. | Dated Filed | Title | Inventor |
|---|---|---|---|---|
| 5408/07421 | 08/074313 | 6/9/93 | Quaternary Ammonium Hydroxide Compositions and Preparation Thereof | Leigh E. Walker |
| 5408/07423 | 08/074312 | 6/9/93 | Quaternary Ammonium Carbonate Compositions and Preparation Thereof | Leigh E. Walker |
| 5408/07424 | 08/074136 | 6/9/93 | Quaternary Ammonium Carboxylate and Borate Compositions and Preparation Thereof | Leigh E. Walker |

FIELD OF THE INVENTION

This invention relates to waterproofing and wood preservation compositions. Polyhydroxyl or polyether hydroxyl esters of fatty acids and polyether hydroxides have been found to be useful as waterproofers for wood substrates. Furthermore, these waterproofers in combination with quaternary ammonium compositions and a solvent are useful as waterproofing wood preservation compositions. Preferred quaternary ammonium composition include $C_1$–$C_{20}$ alkyl or aryl-substituted alkyl, $C_8$–$C_{20}$ alkyl quaternary ammonium chlorides, hydroxides, carbonates, carboxylates, or borates.

BACKGROUND OF THE INVENTION

Quaternary ammonium compounds (quats) and particularly didecyldimethylammonium chloride (DDAC)

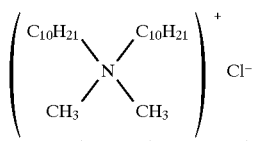

are commonly used as wood preservatives because they possess resistance properties to fungi and termites, to loss of strength, and to electrical sensitivity similar to those of commonly used acidic copper/chromium/arsenic solution (CCA) or ammoniacal copper and arsenic salt solution preservatives. See Proc of the Am. Wood Pres. Assoc., 80: 191–210 (1984). Although chloride quats do not include potentially dangerous heavy metals, didecyldimethylammonium chloride leaches rapidly in soil (Nicholas et al., Forest Prod. J., 41: 41 (1991), and therefore, does require coupling with copper salt.

Findlay et al., U.S. Pat. No. 4,929,454, disclose a method of preserving wood by impregnation with a quaternary ammonium compound and at least one of zinc and copper, wherein the quat anion is chosen from the group consisting of hydroxide, chloride, bromide, nitrate, bisulfate, acetate, bicarbonate, and carbonate, formate, borate and fatty acids. These quats have distinct environmental and safety advantages over commonly used acidic copper/chromium/arsenic solution (CCA) or ammoniacal copper and arsenic salt solution preservatives in that potentially dangerous heavy metals are not included. The Findlay et al. quats require copper or zinc in order to render them relatively insoluble and to prevent them from leaching out of a treated substrate. The use of copper or zinc in the above formulations may yet raise environmental and corrosion concerns.

Additionally, didecyldimethylammonium chloride tends to absorb preferentially to the surface of the wood and does not uniformly treat the whole substrate. Finally, DDAC treated wood shows surface erosion or ages upon exposure to light. See Preston et al., Proc. Am. Wood Pres. Assoc., 83: 331 (1987).

The biocidal activities of various chloride quats against bacteria, fungi, and algae are tabulated in Cationic Surfactants, E. Jungerman Ed., pp. 56–57, Marcel Dekker, Inc., 1969. Nicholas, "Interaction of Preservatives with Wood," Chemistry of Solid Wood, Advance in Chemistry Series #207, Powell ed., (A.C.S. 1984) notes that didecyldimethyl ammonium compounds and particularly DDAC are potential biocides. Preston, J.A.O.C.S. 60: 567 (1983) concurs and suggests that maximum fungitoxicity is exhibited with dialkyldimethyl compounds having $C_{10}$–$C_{12}$ alkyl groups. Butcher et al., Chem Abstracts No. 91: 152627b, suggests that the presence of an acid or a base can affect the activity of didecyldimethyl-ammonium quats.

Didecyldimethylammonium acetate was used as a phase transfer catalyst for an oxidation in Chem Abstracts No. 97: 9175. A wood preservative was prepared by autoclaving didecylmethylamine with gluconic acid and ethylene oxide in isopropanol to yield $(C_{10}H_{21})_2CH_3N\ ((CH_2)_2O)^+$ gluconate in Chem Abstracts No. 109: 124403x, while disinfectant solutions were prepared by exchanging a benzylammonium chloride with a chlorhexidene gluconate in Chem Abstracts No. 103: 109954f.

Biocidal compositions which include quaternary ammonium compounds of the formula $R^1N^+R^2R^3R^4X^-$, wherein at least one of $R^1$, $R^2$, or $R^3$ is a $C_8$–$C_{30}$ alkyl or alkenyl group and the remainder of $R^1$, $R^2$ or $R^3$ is methyl, ethyl, $CH_2Ph$ or 4-pyridylmethyl; $R^4$ is methyl or ethyl; and X is an anion of an acid having a $C_7$ or greater hydrophobic group, were disclosed in Chem Abstracts Nos. 113:154360f and 113:153776j. Chem Abstracts No. 112:79768u discloses compounds of the formula $R^1R^2R^3R^4N^+X^-$, wherein $R^1$, $R^2$, and $R^3$ are methyl, ethyl, benzoyl, 4-pyridinomethyl and at least one is $C_8$–$C_{30}$ alkyl or alkenyl; $R^4$ is methyl or ethyl; and X is a counter anion of acids having $C_7$ or greater hydrophobic groups. Dimethyldidecylammonium dodecyl-benzenesulfonate was demonstrated to impart long term rot resistance to wood without causing rust, while the chloride salts of similar compounds were demonstrated to cause rust.

Patton et al., U.S. Pat. No. 5,004,760, disclose polymeric foams incorporating various dialkyldimethylammonium carboxylates such as didecyldimethylammonium poly (ethylene/acetate) and the like.

Quaternary ammonium compounds (quats) are typically prepared by the reaction:

$$R^1R^2R^3N + R^4X \rightarrow R^1R^2R^3R^4NX \qquad \text{(II)}$$

wherein X is a halogen, a sulfate, a sulfo compound, or the like. When at least one of $R^1$, $R^2$, $R^3$, or $R^4$ is $C_{12}$ or longer, the product is an inert soap. Many of the inert soaps have biocidal activity against bacteria, fungi, algae, and related organisms.

Reaction (II) above is limited by the reactant $R^4X$ because $R^4$ must react with tertiary amines. For example, methyl chloride ($R^4X = CH_3Cl$) will react with a tertiary amine at less than 100° C. to yield a quaternary compound $R_3N^+CH_3$ $Cl^-$, while methanol or methyl acetate ($R^4X = CH_3OH$ or $CH_3COOCH_3$) will not, under similar reaction conditions.

General quaternary ammonium compounds with a sulfo group are easily prepared either by the reaction of a sulfate compound with a tertiary amine (III) or by a double exchange (IV).

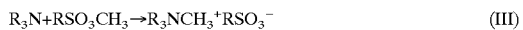

$$R_3N + RSO_3CH_3 \rightarrow R_3NCH_3^+RSO_3^- \qquad \text{(III)}$$

$$R_3N^+CH_3\ Cl^- + RSO_3^-Na^+ \rightarrow R_3NCH_3^+RSO_3^- + NaCl \qquad \text{(IV)}$$

If trimethylamine is heated with carbon dioxide and methanol above 200° C. and at 85 to 95 atmospheres, the carbonate quat, bis-tetramethylammonium carbonate, is prepared. *Industrial Organic Nitrogen Compounds,* Astle Ed. p 66, Reinhold Inc, 1961. However, this reaction is limited to the methyl compound because higher homologs decompose to olefins by the Hofman elimination reaction. See, *Organic Reactions,* 11, Chptr. 5, 377, Krieger Publishing Co., 1975.

Chem Abst. 110: 212114 (1989) suggests that dimethyl carbonate will react with triethylamine in methanol in twelve hours at 115° C. and under pressure to yield a methyl carbonate ester quat.

Chem Abst. 114: 24824 (1991) discloses that 6-hydroxy- or hexyl-dimethylamine reacts with dimethyl carbonate to yield a carbonate ester quat.

Quaternary ammonium hydroxides (hydroxy quats), an intermediate in the reaction scheme of the present invention, are currently prepared by the reaction of quaternary ammonium iodide with silver oxide (V).

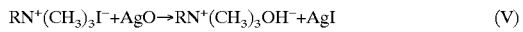

$$RN^+(CH_3)_3I^- + AgO \rightarrow RN^+(CH_3)_3OH^- + AgI \qquad \text{(V)}$$

However, this reaction is costly, and it is difficult to recover the silver reagent. See, *Organic Reactions,* 11: Chptr 5, pp. 376–377, Krieger Publishing Co., 1975.

In an olefin synthesis, it has been suggested to treat a quaternary salt with aqueous sodium or potassium followed by pyrolysis in order to form the hydroxy quat and then to decompose the hydroxy quat directly. However, in this method the hydroxy quat is not isolated and the conditions for its preparation are undesirable. See, *Organic Reactions,* 11: Chptr 5, pp. 376–377, Krieger Publishing Co., 1975.

Talmon et al., *Science,* 221, 1047 (1983), have used an ion exchange resin to convert didecyldimethylammonium bromide to didecyldimethylammonium hydroxide (VI).

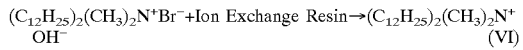

$$(C_{12}H_{25})_2(CH_3)_2N^+Br^- + \text{Ion Exchange Resin} \rightarrow (C_{12}H_{25})_2(CH_3)_2N^+OH^- \qquad \text{(VI)}$$

However, 50 ml of ion exchange resin and two treatment steps were required to convert 3 grams of quaternary ammonium chloride to the corresponding hydroxide. Talmon et al. state that the hydroxy quat can be reacted with acids to make quats with different anions, and they have prepared didodecyldimethylammonium (DDDA) acetate, DDDA-formate, DDDA-propionate, DDDA-butyrate, DDDA-oxalate, DDDA-acrylate, DDDA-tartrate, DDDA-benzoate, and DDDA-octanoate. See also, *Organic Synthesis,* Collective Volume VI, 552, John Wiley Inc., 1988; Brady et al., *J. Am. Chem. Soc.,* 106: 4280–4282, 1984; Brady et al., *J. Phys. Chem.,* 90: 9, 1853–1859, 1986; Miller et al., *J. Phys. Chem,* 91: 1, 323–325, 1989; Radlinske et al., *Colloids and Surfaces,* 46: 213–230, 1990.

Distearyldimethylammonium gluconate was prepared via ion exchange and subsequent reaction with an organic acid in Chem Abstracts No. 75: 119170U. Miller et al, *Langmuir,* 4: 1363 (1988) prepared ditetradecyldimethylammonium acetate by ion exchange from a bromide.

Alternatively, quaternary ammonium hydroxide compositions have been prepared by treating a haloquat in an electro-chemical cell with special cation exchange diaphragms between the cells. The hydroxy quat collects at one electrode, and the halide collects at the other. Hydroxy quats, $R^1R^2R^3R^4N^+OH^-$, wherein the R groups were $C_1$–$C_4$, were treated with carboxylic acids to make asymmetric quats that were used as capacitor driving electrolytes. See, Japanese Patent Publication No. 02-106,915 and Awata et al., *Chemistry. Letters,* 371 (1985). Awata et al. placed carboxylic acids in the cathode cell to react with tetraethylammonium hydroxide as it was formed.

Japanese Patent Publication No. 01-272-363 discloses the preparation of relatively low yields of tetraethylammonium hydroxide by reacting triethylamine with diethyl sulfate, heating the resultant quat with sulfuric acid to yield the sulfate quat, and reacting the sulfate quat with barium hydroxide to yield the short chain quat, tetraethylammonium hydroxide, and barium sulfate.

Di $C_8$–$C_{12}$ alkyl quaternary ammonium hydroxides prepared by ion exchange were used as strong bases to digest animal tissue by Bush et al., French Patent Publication No. 1,518,427.

Akzo discloses that the addition of a metallic hydroxide to a quaternary ammonium chloride such as didecyldimethylammonium chloride, in an aqueous medium, results in an equilibrium mixture of quaternary ammonium chloride and quaternary ammonium hydroxide (VI). This reaction can be driven to the right by the use of isopropanol as a solvent.

$$(R_4N)Cl + KOH \rightleftharpoons (R_4N)OH + KCl \qquad \text{(VII)}$$

Akzo further discloses that the addition of a soap to a quaternary ammonium chloride yields a quaternary ammonium carboxylate (VII).

$$(R_4N)Cl + R^1COONa \rightarrow (R_4N)(OOCR^1) + NaCl \qquad \text{(VIIA)}$$

Jordan et al., U.S. Pat. No. 3,281,458, disclose the preparation of dioctadecyldimethylammonium humate, ditallowdimethylammonium humate, dipentadecyldimethylammonium humate, and didodecyldimethylammonium humate by reacting humic acid, lignite, aqueous sodium hydroxide and a chloride quat.

Finally, Nakama et al., J.A.C.O.S., 67: 717 (1990) report the interaction between anionic and cationic surfactant and particularly sodium laureate and stearyltrimethylammonium chloride, while Linderborg, U.S. Pat. No. 4,585,795, disclose the use of synergistic mixtures of the alkali metal salt of certain biocidal organic acids, quaternary ammonium chlorides, and alkyl-pyridinium chlorides as control agents for short-term protection of timber against sapstain fungi and mildew.

Typically, quaternary ammonium compounds migrate or leach from wood under wet conditions, however. Common waterproofing compositions have not proven compatible with the quaternary ammonium compounds typically used in the industry, and therefore, they are not commonly used to hinder the leaching of these quats.

Typical waterproofers are waxes, lower molecular weight polyolefins, or dispersions or solutions thereof in hydrocarbon solvents. However, quaternary compositions, including those useful in the present invention, typically are water soluble. Generally, they are not soluble in these typical waterproofer solvent systems and are not compatible with emulsified or dispersed waterproofers.

It has now been discovered that $C_1$–$C_{20}$ alkyl or aryl-substituted alkyl, $C_8$–$C_{20}$ alkyl, and particularly di $C_8$–$C_{12}$ alkyl, quaternary ammonium hydroxides, carbonates, carboxylates, and borates including those prepared by the methods described herein, are compatible with newly discovered polyhydroxyl or polyetherhydroxyl esters of fatty acids or polyether hydroxide waterproofers. Waterproofing and wood preservative systems prepared from the waterproofers or waterproofers and quats described herein exhibit enhanced resistance to leaching and meet waterproofing standards for heavy duty, ground, or millwork applications.

BRIEF DESCRIPTION OF THE DRAWING

FIG. 1A is a graphic comparison of leaching of waterproofer containing wood preservative systems according to the present invention and wood preservative systems without waterproofer.

SUMMARY OF THE INVENTION

Figure 1B:
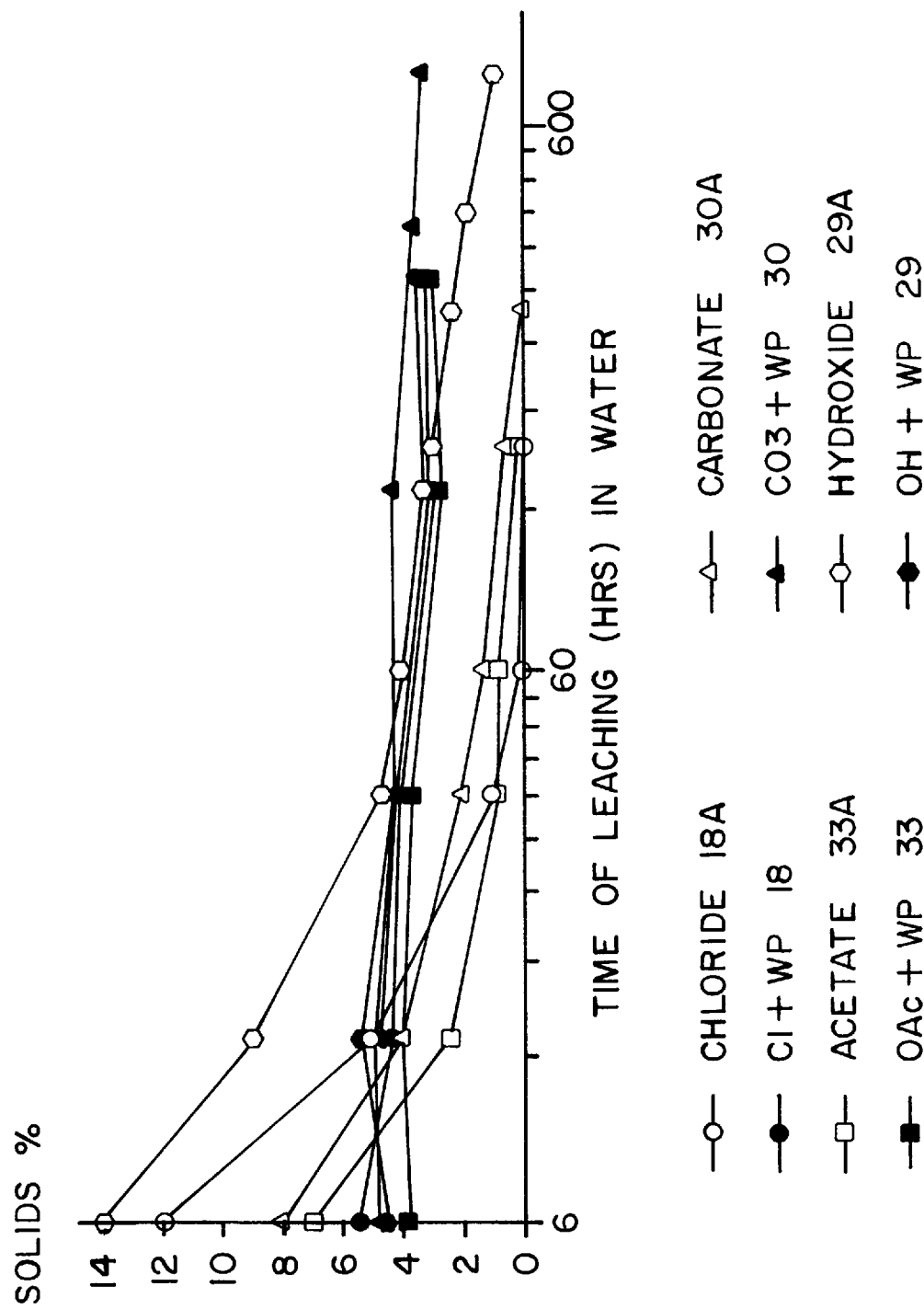
FIG. 1B is an enlarged section of FIG. 1A.

Waterproofer compositions are provided. These waterproofers include (A) compositions having the formula

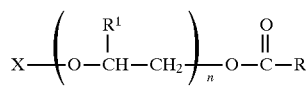 (VIII)

wherein:

X is hydrogen or

R and $R^2$ independently are a saturated or unsaturated, substituted or unsubstituted, interrupted or uninterrupted $C_9$–$C_{50}$ group;

$R^1$ is hydrogen or a methyl group; and n is an integer from 1 to 10.

(B) compositions having the formula:

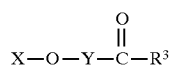 (IX)

wherein:

X is hydrogen or

Y is substituted or unsubstituted

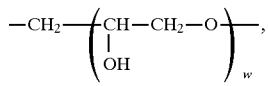

substituted or unsubstituted

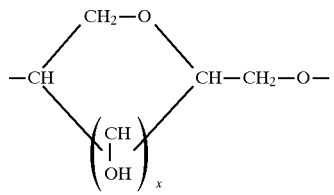

or an enantiomer thereof, or substituted or unsubstituted

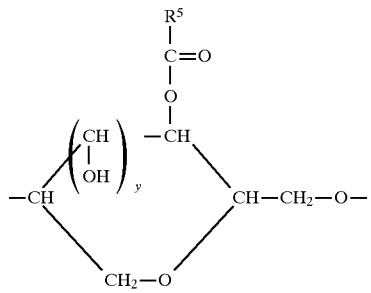

of an enantiomer thereof;

$R^3$, $R^4$, and $R^5$ independently are a saturated or unsaturated, substituted or unsubstituted, interrupted or uninterrupted $C_9$–$C_{50}$ group;

w is an integer from 1 to 10; and x and y are 0, 1, or 2;

(C) compositions having the formula:

 (X)

wherein:

$R^6$ is a saturated or unsaturated, substituted or unsubstituted, interrupted or uninterrupted $C_6$–$C_{30}$ group; and p is an integer from 1 to 30; or (D) any combination of compositions (A), (B), and (C).

Also contemplated by the present invention are the waterproofer systems comprising (A) a waterproofer enhancing amount of any of the waterproofer compositions (A), (B), (C), or (D) above; and (B) a solvent.

In a preferred embodiment, waterproofer, wood preservative systems comprising (A) a waterproofing and compatability enhancing amount of a waterproofer composition as described above;

(B) a biocidal effective amount of at least one $C_1$–$C_{20}$ alkyl or aryl-substituted alkyl, $C_8$–$C_{20}$ alkyl quaternary ammonium compositions selected from the group consisting of quaternary ammonium chlorides, hydroxides, carbonates, carboxylates, borates, or any combination thereof; and (C) a solvent, are provided.

Preferred hydroxide quats are di $C_8$–$C_{12}$ alkyl quaternary ammonium hydroxides. Preferred carbonate quats are those having the formula

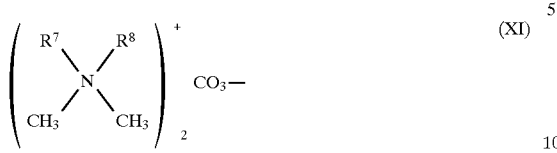

wherein $R^7$ is a $C_1$–$C_{20}$ alkyl or aryl-substituted alkyl group and $R^8$ is a $C_8$–$C_{12}$ alkyl group or a mixture of (a) at least one di $C_8$–$C_{12}$ alkyl quaternary ammonium carbonate having the formula

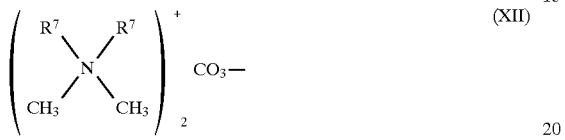

wherein $R^7$ is a $C_8$–$C_{12}$ alkyl group; and (b)(1) at least one di $C_8$–$C_{12}$ alkyl quaternary ammonium bicarbonate having the formula

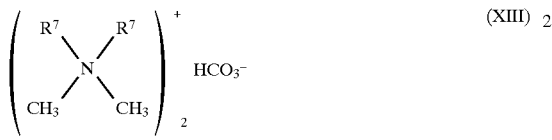

wherein $R^7$ is the same or a different $C_8$–$C_{12}$ alkyl group as in (a); or (2) at least one di $C_8$–$C_{12}$ alkyl quaternary ammonium metal carbonate having the formula

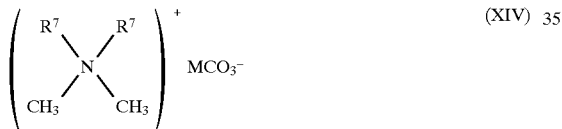

wherein $R^7$ is the same or a different $C_8$–$C_{12}$ alkyl group as in (a) or (b) and M is a non-coupler metal, or (3) a combination of (b)(1) and (b)(2). Preferred quaternary ammonium carboxylates are those having the formula

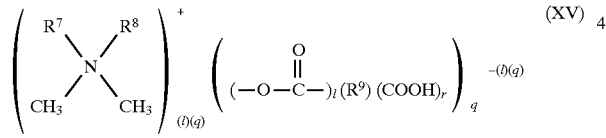

wherein $R^7$ is a $C_1$–$C_{20}$ alkyl or aryl-substituted alkyl group; $R^8$ is a $C_8$–$C_{20}$ alkyl group; $R^9$ is a substituted or unsubstituted, interrupted or uninterrupted, $C_1$–$C_{100}$ group; l and q independently are 1, 2, or 3, and (l)(q) is 1, 2, or 3; and r is 0 or an integer from 1 to 50. Preferred quaternary ammonium borates are those having the formula

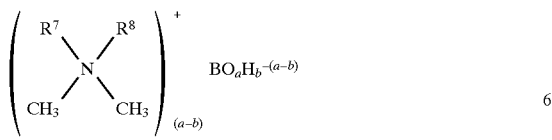

wherein $R^7$ is a $C_1$–$C_{20}$ alkyl or aryl-substituted alkyl group; $R^8$ is a $C_8$–$C_{20}$ alkyl group, a is 2 or 3, but when a is 2, b is 0 or 1 and when a is 3, b is 0, 1 or 2.

In further embodiments, methods for waterproofing or waterproofing and preserving a wood substrate are provided wherein the substrate is treated with the waterproofer or waterproofer preservative systems above.

DETAILED DESCRIPTION OF THE INVENTION

I. Waterproofers

The polyhydroxyl or polyether hydroxyl fatty acid ester or the polyether hydroxide waterproofers of the present invention are soluble in both aqueous and organic solvent systems. Furthermore, they render the water-soluble quats described herein useful in aqueous or organic systems as well. This occurs despite the fact that these quats alone, i.e. without the present waterproofers, are relatively insoluble in organic solvents, emulsions or dispersions., i.e. they are not generally useful in preserving wood when in an organic solvent.

The waterproofers of the present invention include compositions of the formula:

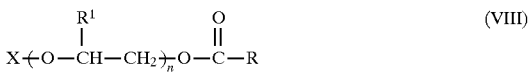

wherein:

X is hydrogen or

R and $R^2$ independently are a saturated or unsaturated, substituted or unsubstituted, interrupted or uninterrupted $C_9$–$C_{50}$ group;

$R^1$ is hydrogen or a methyl group; and n is an integer from 1 to 10.

Saturated $C_9$–$C_{50}$ groups include $C_9$–$C_{50}$ straight chain, branched, or cycloalkyl groups. Unsaturated $C_9$–$C_{50}$ groups include those groups having one or more double or triple bonds or combinations thereof including acyclic groups (including straight chain or branched), cyclic groups, or combinations thereof. In combinations, unsaturation may occur in the cyclic portion, the acyclic portion, or both. Substituted R or $R^2$ groups can be substituted with one or more saturated or unsaturated carbon groups with the proviso that the total number of carbon atoms in the R or $R^2$ group ranges from 9 to 50. These substitutions can give rise to cyclic R or $R^2$ groups substituted with straight chain or branched, saturated or unsaturated acyclic groups and acyclic R or $R^2$ groups substituted with saturated or unsaturated cyclic groups. Substituted R or $R^2$ groups can alternatively or additionally be substituted with one or more oxygen or boron atoms or sulfate groups. Interrupted groups are interrupted by one or more oxygen or boron atoms or sulfate groups.

Special mention is made of (A) propylene glycol monbstearate, wherein X is hydrogen, R is a $C_{17}$ alkyl group, $R^1$ is a methyl group and n is 1;

(B) polyethylene glycol distearate (PEG 400-DS) wherein X is

R and $R^2$ each are a $C_{17}$ alkyl group, $R^1$ is hydrogen, and n is 8; and (C) glycol monostearate wherein X is hydrogen, R is a $C_{17}$ alkyl group, $R^1$ is hydrogen, and n is 1. Waterproofers also include compositions of the formula

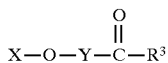

wherein:

X is hydrogen or

Y is substituted or unsubstituted

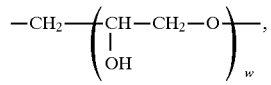

substituted or unsubstituted

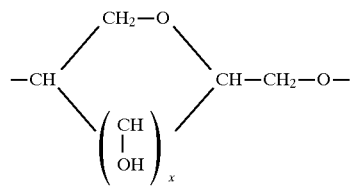

or an enantiomer thereof, or substituted or unsubstituted

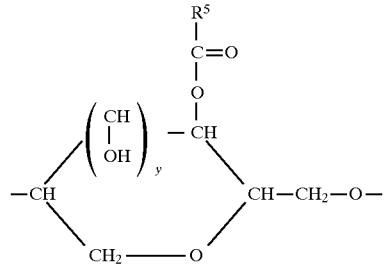

or an enantiomer thereof
wherein $R^3$, $R^4$, and $R^5$ independently are a saturated or unsaturated, substituted or unsubstituted, interrupted or uninterrupted $C_9$–$C_{50}$ group; w is an integer from 1 to 10; and x and y are 0, 1, or 2.

Y groups can be substituted with one or more $C_1$–$C_9$ groups with the proviso that the number of carbon atoms in the Y group ranges from 3 to 12, one or more oxygen or boron atoms or sulfate groups or any combination thereof, and can be interrupted by one or more oxygen or boron atoms or sulfate groups.

Saturated $C_9$–$C_{50}$ groups include $C_9$–$C_{50}$ straight chain, branched, or cycloalkyl groups. Unsaturated $C_9$–$C_{50}$ groups include those groups having one or more double or triple bonds or combinations thereof including acyclic groups (including straight chain or branched), cyclic groups, or combinations thereof unsaturated groups. In combinations, unsaturation may occur in the cyclic portion, the acyclic portion, or both. Substituted $R^3$, $R^4$, or $R^5$ groups can be substituted with one or ore saturated or unsaturated carbon groups with the proviso hat the total number of carbon atoms in the $R^3$, $R^4$, or $R^5$ group ranges from 9 to 50. These substitutions can give rise to cyclic $R^3$, $R^4$, or $R^5$ groups substituted with straight chain or branched, saturated or unsaturated groups and acyclic $R^3$, $R^4$ or $R^5$ groups substituted with saturated or unsaturated cyclic groups. Substituted $R^3$, $R^4$, or $R^5$ groups can alternatively or additionally be substituted with one or more oxygen or boron atoms or sulfate groups. Interrupted groups are interrupted with one or more oxygen or boron atoms or sulfate groups.

Special mention is made of
(A) glycerol monostearate wherein Y is

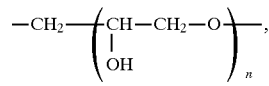

X is hydrogen, $R^3$ is a $C_{17}$ alkyl group, and n is 1;
(B) glycerol monolaurate wherein Y is

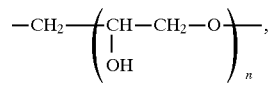

X is hydrogen, $R^3$ is a $C_{11}$ alkyl group, and n is 1; and
(C) cyclic polyhydroxides such as
(1) sorbitan monostearate wherein Y is

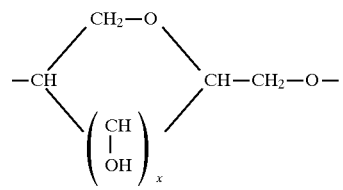

or an enantiomer thereof X is hydrogen, $R^3$ is a $C_{17}$ alkyl group, and x is 2, or
(2) sorbitan tristearate wherein Y is

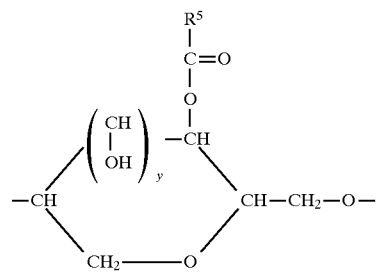

or an enantiomer thereof,
X is

$R^3$, $R^4$, and $R^5$ each are a $C_{17}$ alkyl group, and y is 1.
The waterproofers of the present invention also include compositions of the formula

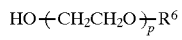 (X)

wherein $R^6$ is a saturated or unsaturated, substituted or unsubstituted, interrupted or uninterrupted $C_6$–$C_{30}$ group, and p is an integer from 1 to 30.

Saturated $C_6$–$C_{30}$ groups include $C_6$–$C_{30}$ straight chain, branched, or cycloalkyl groups. Unsaturated $C_6$–$C_{30}$ groups include those groups having one or more double or triple bonds or combinations thereof including acyclic groups (including straight chain or branched), cyclic groups, or combinations thereof unsaturated groups. In combinations, unsaturation may occur in the cyclic portion, the acyclic portion, or both. Substituted $R^6$ groups can be substituted with one or more saturated or unsaturated carbon groups with the proviso that the total number of carbon atoms in the $R^6$ group ranges from 6 to 30. These substitutions can give rise to cyclic $R^6$ groups substituted with straight chain or branched, saturated or unsaturated acyclic groups and acyclic $R^6$ groups substituted with saturated or unsaturated cyclic groups. Substituted $R^6$ groups can alternatively or additionally be substituted with one or more oxygen or boron atoms or sulfate groups. Interrupted groups are interrupted by one or more oxygen or boron atoms or sulfate groups.

Special mention is made of compositions where $R^6$ is either p-nonylphenyl or $C_n$ alkyl, and p is 4.

Also contemplated by the present invention are combinations of any of the above waterproofers.

These waterproofers hinder migration of the quat molecules from a substrate under wet conditions. Furthermore, where surface corrosion problems are related to the water holding properties of the quat, the waterproofer displaces or prevents the entry of water.

II. Quaternary Ammonium Composition Component

A. Quaternary Ammonium Hydroxide

Although any quaternary ammonium hydroxides are suitable for use in the present invention, quaternary ammonium hydroxides (hydroxy quats) having the formula

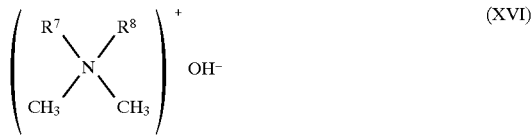

(XVI)

wherein $R^7$ is a $C_1$–$C_{20}$ alkyl or aryl-substituted alkyl group, $R^8$ is a $C_8$–$C_{20}$ alkyl group, and preferably $R^7$ is the same as $R^8$ and $R^7$ is a $C_8$–$C_{12}$ alkyl group, are preferred.

Special mention is made of hydroxy quats wherein $R^7$ is a methyl, $C_8$ alkyl, $C_9$ isoalkyl, $C_{10}$ alkyl, $C_{12}$ alkyl, $C_{14}$ alkyl, $C_{16}$ alkyl, or benzyl group; and $R^8$ is a $C_{10}$ alkyl, $C_{12}$, $C_{14}$ alkyl or $C_{16}$ alkyl group. Most preferred hydroxy quats are didecyldimethylammonium hydroxide wherein $R^7$ and $R^8$ are a $C_{10}$ alkyl group and most preferably an n-$C_{10}$ group.

Didecyldimethylammonium hydroxide, when observed in a 70 to 80 percent by weight solution in a 50 percent by weight alcohol/50 percent by weight water solvent, is a yellow/orange liquid. This formulation has a flash point of about 134° F., and it is a highly alkaline material that reacts with the phenolic OH of lignin.

Quaternary ammonium hydroxides useful in the present invention are preferably prepared according to the reaction illustrated below.

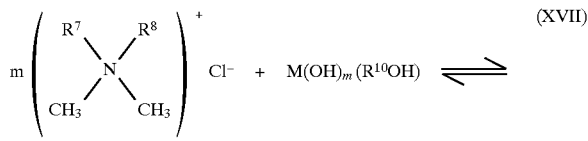

(XVII)

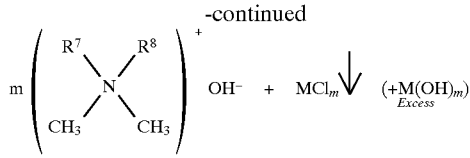

wherein $R^7$ is a $C_1$–$C_{20}$ alkyl or aryl-substituted alkyl group; $R^8$ is a $C_8$–$C_{20}$ alkyl group; $R^{10}$ is a straight chain $C_1$–$C_4$ alkyl group; M is a mono-, di-, or trivalent metal; and m is one if M is monovalent, two if M is divalent, and three if M is trivalent. Preferably $R^7$ is the same as $R^8$, i.e. a $C_8$–$C_{12}$ alkyl group.

Many $C_1$–$C_{20}$ alkyl or aryl-substituted alkyl, $C_8$–$C_{20}$ alkyl quaternary ammonium chlorides are suitable reactants, but di $C_8$–$C_{12}$ alkyl quaternary ammonium chloride is preferred, and didecyldimethylammonium chloride, and particularly, di-n-decyldimethylammonium chloride is most preferred. The selections of the $R^7$ and $R^8$ substituents of the chloride quat reactant are determinative of the hydroxy quat product.

Special mention is also made of processes wherein $R^7$ is a methyl, butyl, $C_8$ alkyl, $C_9$ isoalkyl, $C_{10}$ alkyl, $C_{12}$ alkyl, $C_{14}$ alkyl or benzyl group; and $R^8$ is a $C_{10}$ alkyl, $C_{12}$ alkyl, $C_{14}$ alkyl or $C_{16}$ alkyl group.

The metal hydroxide reactant is a mono-, bi-, or trivalent metal hydroxide, preferably a monovalent metal hydroxide, and most preferably an alkali metal hydroxide such as sodium hydroxide or potassium hydroxide. Special mention is made of potassium hydroxide. The metal chloride reaction product will precipitate and is easily removed, i.e. by filtration or the like, yielding a hydroxy quat/solvent reaction product. The hydroxy quat can be separated therefrom by drying or the like.

The reaction is conducted in a solvent which comprises a $C_1$–$C_4$ normal alcohol. Preferably, the solvent is ethanol, and most preferably, anhydrous ethanol.

The amount of metal hydroxide reactant typically is a stoichiometric amount with respect to the quaternary ammonium chloride reactant. Therefore, on a theoretical basis and if the reaction were complete and unequilibrated, there would be no excess of metal hydroxide reactant upon completion of the reaction. In practice, yield when using a stoichiometric amount of metal hydroxide reactant will range from about 65% to about 95%, but will vary, dependent in part upon the particular metal hydroxide reactant.

Yield can be further improved over conventional methods by utilization of a stoichiometric excess of metal hydroxide ranging from about 2% to about 20% excess. If an excess of metal hydroxide is used, yield will be increased to from about 95% to about 99%, again varying as above.

The unreacted metal hydroxide is soluble in the hydroxy quat/solvent mixture. Any excess or unreacted metal hydroxide should be removed after the reaction is completed, and is preferably precipitated by subsequent reaction with carbon dioxide to yield the corresponding metal carbonate. The carbonate is insoluble in the hydroxy quat/solvent mixture and is easily removed, i.e. by filtration or the like. Alternatively, a solid metal bicarbonate, in which the metal corresponds to the metal of the metal hydroxide, can be added and slurried with the hydroxy quat/solvent mixture. The soluble metal hydroxide reacts with solid bicarbonate to yield the insoluble metal carbonate. The metal carbonate does not react further with the hydroxy quat.

Mixing, adding, and reacting of the components in the preparation of these hydroxy quats can be accomplished by conventional means known to those of ordinary skill in the art. The order of addition of reactants or solvent does not affect the process. Reactants and/or solvent can be added sequentially or simultaneously in any suitable reaction vessel.

Typically, the reactants and solvent will be stirred and heated to from about 20° C. to about 70° C. and held at that temperature for a period of from about 1 hour to about 5 hours. The reaction mixture is then cooled, first to room temperature and then to about 0° C. where it is held for about 1 hour to about 2 hours. Any precipitated metal chloride is collected as is known in the art, i.e. such as by filtration.

Alternatively, the reactants and solvent can be stirred at a slightly elevated temperature, i.e. from about 20° C. to about 40° C., to yield the hydroxy quat/solvent mixture. Hydroxy quat can be separated as above.

B. Quaternary Ammonium Carbonate

Although any quaternary ammonium carbonates are suitable for use in the present invention, preferred carbonate quats have the formula

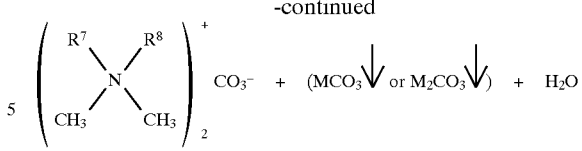

(XI)

wherein $R^7$ is a $C_1$–$C_{20}$ alkyl or aryl-substituted alkyl group, $R^8$ is a $C_8$–$C_{20}$ alkyl group, and preferably $R^7$ and $R^8$ are the same $C_8$–$C_{12}$ alkyl group.

Special mention is made of carbonate quats wherein $R^7$ is a methyl, $C_8$ alkyl, $C_9$ isoalkyl, $C_{10}$ alkyl, $C_{12}$ alkyl, $C_{14}$ alkyl, $C_{16}$ alkyl, or benzyl group; and $R^8$ is a $C_{10}$ alkyl, $C_{12}$ alkyl, $C_{14}$ alkyl, or $C_{16}$ alkyl group.

Most preferred carbonate quats are didecyldimethylammonium carbonate wherein $R^7$ and $R^8$ are a $C_{10}$ alkyl group and preferably an n-$C_{10}$ alkyl group. Didecyldimethylammonium carbonate, when observed as a 70–80 percent by weight solution is a yellow/orange liquid that has a slightly fruity odor. This formulation has a flash point of about 160° F, and it reacts with carboxyl containing compounds.

One or more of these carbonate quats alone or in combination with the corresponding bicarbonate quat(s) and/or metal carbonate salt(s), preferably potassium carbonate salt, can be formulated in the present waterproofer, wood preservative systems.

Although certain carbonate quats can be prepared by a variety of methods, preferably, the carbonate quats used in the present invention are prepared by an indirect synthesis method.

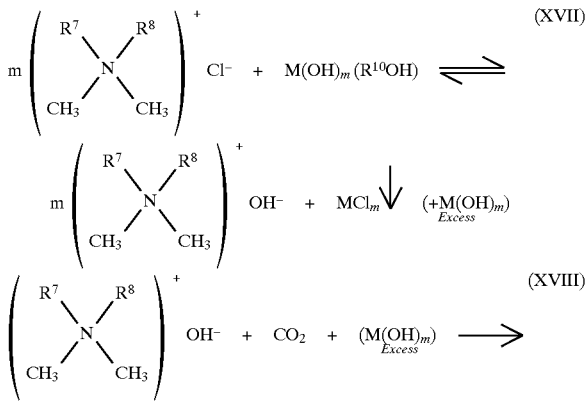

-continued

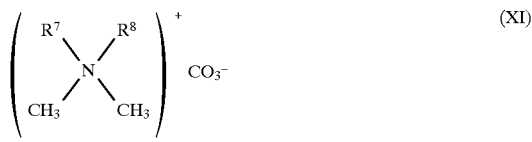

wherein $R^7$ is a $C_1$–$C_{20}$ alkyl or aryl-substituted alkyl group; $R^8$ is a $C_8$–$C_{20}$ alkyl group; and preferably $R^7$ is the same as $R^8$ and $R^7$ is a $C_8$–$C_{12}$ alkyl group; $R^{10}$ is a straight chain $C_1$–$C_4$ alkyl group; M is a mono-, bi-, tri-valent metal, preferably a mono-valent metal, and most preferably an alkali metal; and m is 1 if M is mono-valent, 2 if M is di-valent, and 3 if M is tri-valent.

A $C_1$–$C_{20}$ alkyl or aryl-substituted alkyl, $C_8$–$C_{20}$ alkyl, and preferably a di $C_8$–$C_{12}$ alkyl, quaternary ammonium chloride is used as a starting material and is reacted with a metal hydroxide to yield a $C_1$–$C_{20}$ alkyl or aryl-substituted alkyl, $C_8$–$C_{20}$ alkyl, and preferably a di $C_8$–$C_{12}$ alkyl, quaternary ammonium hydroxide intermediate. The hydroxy quat intermediate(s) and any excess metal hydroxide are then reacted with carbon dioxide to yield the carbonate quat(s) and the metal carbonate.

Many di $C_8$–$C_{12}$ alkyl quaternary ammonium chlorides are suitable reactants to prepare the intermediate hydroxy quat and are described above. The selections of the $R^7$ and $R^8$ substituents of the chloride quat reactant are determinative of the hydroxy quat intermediate, and therefore, of the carbonate quat product.

The metal hydroxide reactant is also as described above.

The metal chloride first step reaction product will precipitate and is easily removed, i.e. by filtration or the like, yielding a hydroxy quat/solvent reaction product. The hydroxy quat can be separated therefrom by drying or the like, if desired.

The first reaction (XVII) is conducted in a solvent as described above, and the amount of metal hydroxide reactant is as described above.

Hydroxy quat and any unreacted metal hydroxide are then reacted with at least a stoichiometric equivalent of carbon dioxide to yield the quaternary ammonium carbonate(s), and if any unreacted metal hydroxide is present, the metal carbonate(s). The conversion of the metal hydroxide to the metal carbonate is the preferred reaction of the two carbonations and will proceed more rapidly. The metal carbonate will precipitate and can be separated easily, i.e. by filtration or the like, leaving the stable carbonate quat(s) or carbonate quat(s)/solvent reaction product.

The carbonation step can also produce the bicarbonate quat or the metal carbonate quat as byproducts. The carbonate quat alone or in combination with the bicarbonate quat and/or the metal carbonate quat are suitable for use in the metal coupler-free wood preservative systems of the present invention. These carbonate quats or carbonate/bicarbonate/metal carbonate compositions, do not require a metal coupler for stabilization in a wood substrate. Completely metal-free wood preservative systems are preferred. However, if a metal carbonate quat is included in the system, preferably the metal is not a metal currently used as a coupler, and most preferably, it is an alkali metal and does not pose environmental or corrosion hazards or concerns.

Mixing, adding, and reacting of the components in the preparation of these carbonate quats can be accomplished by conventional means known to those of ordinary skill in the art. The order of addition of reactants or solvent in any individual step does not affect the process. Reactants and/or solvent can be added sequentially or simultaneously in any suitable reaction vessel. For example, the metal hydroxide may be dissolved in alcohol and the resultant mixture added to the chloride quat or the chloride quat may be dissolved in alcohol and the metal hydroxide added to the resultant mixture.

The carbon dioxide is generally bubbled for a suitable period known to those of ordinary skill in the art through the hydroxy quat/solvent supernatant after the metal chloride precipitate has been separated. Alternatively, the carbon dioxide can be added as solid dry ice directly to the hydroxy quat. Typically, this time varies from about 0.5 hour to about 1 hour at ambient temperature. Any precipitated metal carbonate is collected as is known in the art, i.e. such as by filtration.

C. Quaternary Ammonium Carboxylate

Although any quaternary ammonium carboxylates are suitable for use in the present invention, preferred carboxylate quats have the formula

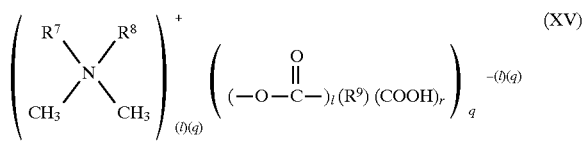

wherein $R^7$ is a $C_1$–$C_{20}$ alkyl or aryl-substituted alkyl group; $R^8$ is a $C_8$–$C_{20}$ alkyl group; but preferably $R^7$ and $R^8$ are the same $C_8$–$C_{12}$ alkyl group; $R^9$ is a substituted or unsubstituted, interrupted or uninterrupted $C_1$–$C_{100}$ group; l and q independently are 1, 2, or 3, and (E)(q) is 1, 2, or 3; and r is 0 or an integer from 1 to 50.

Special mention is also made of carboxylate quats wherein $R^7$ is a methyl, $C_8$ alkyl, $C_9$ isoalkyl, $C_{10}$ alkyl, $C_{12}$ alkyl, $C_{14}$ alkyl or benzyl group; and $R^8$ is a $C_{10}$ alkyl, $C_{12}$ alkyl, $C_{14}$ alkyl or $C_{16}$ alkyl group. Most preferred carboxylate quats are didecyldimethylammonium carboxylates wherein $R^7$ and $R^8$ are a $C_{10}$ alkyl group and most preferably an n-$C_{10}$ alkyl group.

Preferred carboxyl anions are derived from saturated or unsaturated mono- or poly-, including, but not limited to, di- or tri-, carboxylic acids, and particularly $C_1$–$C_{20}$ carboxylic acids, or anhydrides thereof. $R^9$ independently can be substituted, particularly by one or more oxygen or boron atoms or sulfate groups, or interrupted, particularly by one or more oxygen or boron atoms or sulfate groups. Special mention is made of acetic acid, gluconic acid, lauric acid, formic acid, propionic acid, butyric acid, oxalic acid, acrylic acid, tartaric acid, benzoic acid, octanoic acid, and the like. Additionally, the carboxyl group can be derived from polymeric acid. An example of a polyacid is polyacrylic acid. Examples of copolymer acids include, but are not limited to, olefin/carboxylic acid polymers such as poly(ethylene/acrylic acid).

Such acids, including the polymeric or copolymeric acids mentioned above are of the formula

where $R^9$, l, r, and q are defined as above. In polymeric copolymers carboxylic acids, $R^9$ can be represented as $((R^{11})_s(R^{12})_t)$ giving

where $R^{11}$ and $R^{12}$ independently are substituted or unsubstituted, interrupted or uninterrupted as above $C_1$–$C_{100}$ groups and s and t independently are integers from 1 to 100.

Preferably, $R^9$, $R^{11}$, and $R^{12}$ independently are alkyl or alkenyl groups.

Although the carboxylate quats can be prepared by a variety of methods, preferably they are prepared by an indirect synthesis, a direct synthesis, or a hydroxy quat/acid synthesis.

The indirect synthesis is illustrated below

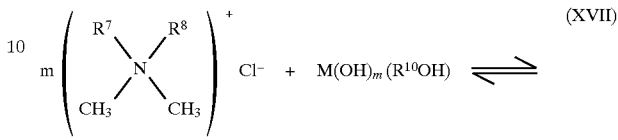

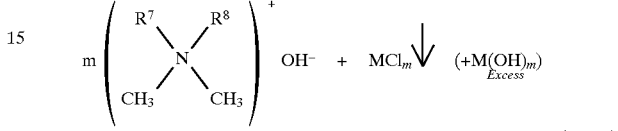

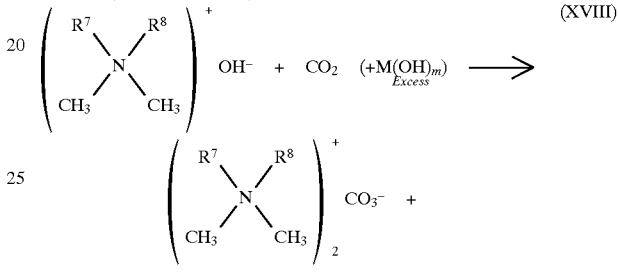

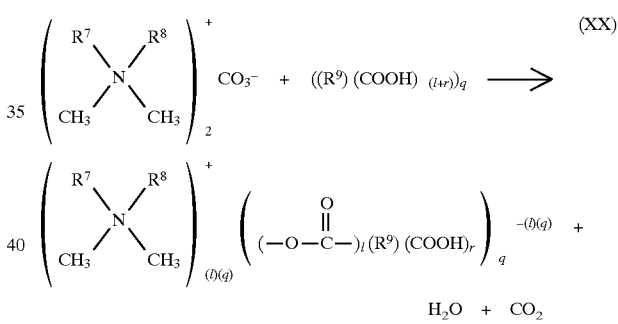

wherein $R^7$ is a $C_1$–$C_{20}$ alkyl or aryl-substituted alkyl group; $R^8$ is a $C_8$–$C_{20}$ alkyl group; and preferably $R^7$ is the same as $R^8$ and $R^8$ is a $C_8$–$C_{12}$ alkyl group; $R^{10}$ is a straight chain $C_1$–$C_4$ alkyl group; $R^9$ is a substituted or unsubstituted, as explained above, interrupted or uninterrupted, as explained above, $C_1$–$C_{100}$ group; l and q independently are 1, 2, or 3 and (l) (q) is 1, 2, or 3; M is a mono-, bi-, tri-valent metal, preferably a monovalent metal, and most preferably an alkali metal; r is 0 or an integer from 1 to 50; and m is 1 if M is mono-valent, 2 if M is di-valent, and 3 if M is tri-valent.

The carboxylate quat is prepared via a carbonate quat intermediate.

A $C_1$–$C_{20}$ alkyl or aryl-substituted alkyl, $C_8$–$C_{20}$ alkyl, and preferably a di $C_8$–$C_{12}$ alkyl, quaternary ammonium chloride is used as a starting material and is reacted with a metal hydroxide to yield a $C_1$–$C_{20}$ alkyl or aryl-substituted alkyl, $C_8$–$C_{20}$ alkyl, and preferably a di $C_8$–$C_{12}$ alkyl, quaternary ammonium hydroxide intermediate as above. The hydroxy quat intermediate(s) and any excess metal hydroxide are then reacted with carbon dioxide to yield the carbonate quat(s) and the metal carbonate(s) as above. The carbonate quat second intermediate(s) is then reacted with at least one carboxylic acid to yield the carboxylate quat(s). The selection of the $C_8$–$C_{12}$ alkyl substituent of the chloride quat reactant is determinative of the hydroxy quat first intermediate, therefore, of the carbonate quat second intermediate, and ultimately, of the cation component of the carboxylate quat product.

The metal hydroxide reactant is described above. The preparation of the hydroxy quat is preferably conducted in a solvent as described above, and the amount of metal hydroxide reactant is described above.

Hydroxy quat and any unreacted metal hydroxide are then reacted with carbon dioxide to yield the quaternary ammonium carbonate(s) as detailed above. The carbonation step can also produce the bicarbonate quat(s) or the metal carbonate quat(s) as by-products.

The carbonate quat second intermediate(s) is then reacted with at least a stoichiometric amount of carboxylic acid(s) to yield the carboxylate quat(s).

The carboxylic acid(s) in reaction (XX) is typically added over a short period of several minutes, and the reaction typically is rapid. The carboxylate quat(s) can be separated or concentrated by filtration or evaporation after a carbon dioxide evolution in this step is completed.

In the indirect synthesis, any acid having a pKa less than that of carbonic acid, i.e., less than 6.4, such as carboxylic, phosphoric, sulfonic acids, and the like, can be reacted with a carbonate quat and displace carbon dioxide.

The addition of ammonia will retard the carbonate quat and acid reaction (XX). For example, if ammonia is added to a mixture of a polyacid and a carbonate quat, the acid-carbonate quat reaction is retarded. However, when ammonia is slowly evaporated, the reaction liberating carbon dioxide may proceed, yielding a compound that is fixed (insoluble) in wood. Similarly, a system of polyacid and acetic acid should yield an insoluble polyacid quat when the acetic acid evaporates.

Alternatively, the carboxylate quats can be prepared by a direct synthesis method. A metal salt of a carboxylic acid is reacted with a $C_1$–$C_{20}$ alkyl or aryl-substituted alkyl, $C_8$–$C_{20}$ alkyl, and preferably a di-$C_8$–$C_{12}$ alkyl, quaternary ammonium chloride, in a double replacement reaction, to yield the carboxylate quat and the metal chloride salt

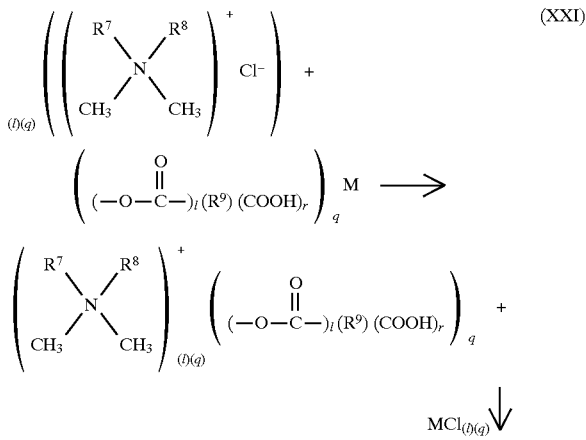

wherein $R^7$, $R^8$, $R^9$, M, l, q, and r are as defined above.

The metal carboxylates are derived from carboxylic acids. The carboxylic acids are as described and detailed above. The metals are mono-, di-, or the tri-valent metals, preferably mono-valent metals and most preferably alkali metals. Special mention is made of potassium and sodium.

Reaction (XXI) can be conducted neat or in a number of solvents including, but not limited to ethanol, acetic acid, or propionic acid. Preferably, the solvent comprises a $C_1$–$C_4$ normal alcohol as described above. Yield will depend on the solvent and the reaction conditions selected, which can be determined by one of ordinary skill in the art through routine experimentation in accordance with this detailed explanation.

The chloride quat starting material is selected as above, and again, its selection is determinative of the cation of the carboxylate quat to be formed.

Finally, a third method for the production of the carboxylate quat(s) includes reacting hydroxy quat(s) with carboxylic acid(s).

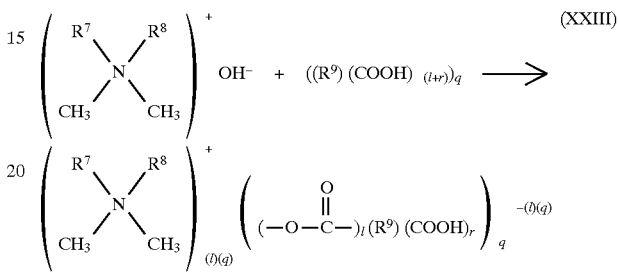

wherein $R^7$, $R^8$, $R^9$, l, l, and r are as defined above.

The hydroxy quat(s), carboxylic acid(s), and carboxylate quat(s) are as described above.

Mixing, adding, and reacting of the components in any of the direct, indirect or hydroxy quat/acid methods can be accomplished by conventional means known to those of ordinary skill in the art. The order of addition of reactants or solvent in any individual step does not affect the process.

D. Quaternary Ammonium Borate

Although any quaternary ammonium borates are suitable for use in the present invention, preferred borate quats have the formula

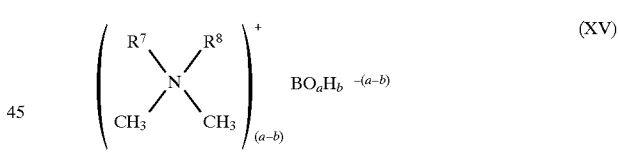

wherein $R^7$ is a $C_1$–$C_{20}$ alkyl or aryl-substituted alkyl group; $R^8$ is a $C_8$–$C_{20}$ alkyl group; but preferably $R^7$ and $R^8$ are the same $C_8$–$C_{12}$ alkyl group; a is 2 or 3, but when a is 2, b is 0 or 1 and when a is 3, b is 0, 1, or 2.

Special mention is also made of borate quats wherein $R^7$ is a methyl, $C_8$ alkyl, $C_9$ isoalkyl, $C_{10}$ alkyl, $C_{12}$ alkyl, $C_{14}$ alkyl or benzyl group; and $R^8$ is a $C_{10}$ alkyl, $C_{12}$ alkyl, $C_{14}$ alkyl or $C_{16}$ alkyl group. Most preferred borate quats are didecyldimethylammonium borates wherein $R^7$ and $R^8$ are a $C_{10}$ alkyl group and most preferably an n-$C_{10}$ alkyl group.

Typically, the production of the borate quat(s) includes reacting hydroxy quat(s) with boric acid.

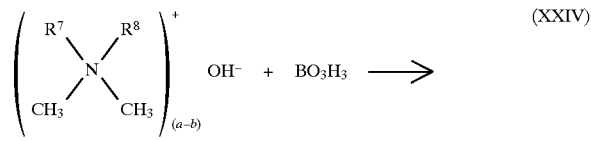

-continued

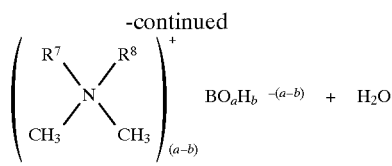

wherein $R^7$, $R^8$, $R^9$, a, and b are as defined above.

Mixing, adding, and reacting of the components in the hydroxy quat/acid method can be accomplished by conventional means known to those of ordinary skill in the art. The order of addition of reactants does not affect the process.

III. Solvents

The waterproofer and waterproofer, preservative systems of the present invention include a suitable solvent including aqueous and non-aqueous solvents. Preferably, the solvent is an aqueous solvent including, but not limited to, water, aqueous alcohol, ammonia water, aqueous acetic acid, and the like, or a combination of any of the foregoing. Organic solvents may also be used. These include, but are not limited to, mineral spirits-based solvents and the like.

IV. Waterproofer Systems and Treatment of Substrates

The amount of waterproofer used in the waterproofer systems of the present invention is a waterproofing enhancing amount, i.e. that amount effective to impart or to increase the water resistance of a substrate treated therewith.

Typically, a waterproofer system will comprise from about 0.1 to about 20 parts by weight of waterproofer and from about 80 to about 99.9 parts by weight of solvent based upon 100 parts by weight of waterproofer and solvent combined. Preferably, the waterproofer system of the present invention will comprise from about 0.2 to about 5 parts by weight of waterproofer and from about 95 to about 99.8 parts by weight of solvent on the same basis.

The components of the waterproofer systems of the present invention are mixed by conventional means known to those skilled in the art. Other conventional additives may be added as required for application to different substrates and for different uses as known to those of ordinary skill in the art. Wood substrates, such as lumber, timber, or the like, can be treated with these systems. Treatment of the substrate is accomplished by any means known to those of ordinary skill in the art including, but not limited to, dipping, soaking, brushing, pressure treating, or the like. The length of treatment time required will vary according to treatment conditions, the selection of which are known to those skilled in the art.

IV. Waterproofer, Wood Preservative Systems and Treatment of Substrates

The amount of waterproofer used in the waterproofer, wood preservative systems of the present invention is a waterproofing and compatabilizing enhancing amount, i.e. that amount effective to impart or to increase the water resistance, leaching resistance, and/or dimensional stability of the waterproofer, wood preservative system and/or the quat and to enhance the compatibility of the quats of the present invention with a solvent.

The amount of quaternary ammonium composition(s) is a biocidal effective amount, i.e. that amount effective to inhibit the growth of or to kill one or more organism that causes wood rot, to inhibit sap stain, or a combination thereof. Such organisms include, but are not limited to, Trametes viride or Trametes versicolor, which cause a white rot; Goeophyllium trabeum, which causes a brown rot; and Aspergillus niger, which causes sap stain/mold.

Typically, a waterproofer, wood preservative system will comprise from about 0.1 to about 15 parts by weight of waterproofer(s), from about 0.1 to about 10 parts by weight of quat(s), and from about 99.8 to about 75 parts by weight of solvent based upon 100 parts by weight of quat, waterproofer, and solvent combined. Preferably, the waterproofer, wood preservative systems of the present invention will comprise from about 0.5 to about 6 parts by weight of quat(s) from about 0.5 to about 8.5 parts by weight of waterproofer(s), and from about 96 to about 85.5 parts by weight of solvent on the same basis.

The components of the waterproofer, wood preservative systems of the present invention are mixed by conventional means known to those skilled in the art preferably to form an emulsion. Preferably, the waterproofer and the quat are melted together. The melt can then be stirred, and warm water (about 40° to 50° C.) added with stirring to yield an emulsion or solution. Emulsions prepared in this manner may be stable for periods of at least one year.

Although other conventional additives including, but not limited to, emulsifiers may be added as required for application to different substrates and for different uses as known to those of ordinary skill in the art, metal stabilizers are not required and, in fact, are not recommended to inhibit leaching of the quat from the substrate. Accordingly, wood substrates, such as lumber, timber, or the like, can be treated with these systems.

Treatment of the substrate is accomplished by any means known to those of ordinary skill in the art including, but not limited to, dipping, soaking, brushing, pressure treating, or the like. The length of treatment required will vary according to treatment conditions, the selection of which are known to those skilled in the art.

The waterproofer, wood preservative systems of the present invention display greater resistance to leaching and greater waterproofing properties, as indicated by swell index, than wood preservatives currently used in the industry. Resistance to leaching is defined as retention of a biocidal effective amount, and preferably at least about 2% by weight, of quat in the substrate over a prolonged period of at least about 100 hours and preferably about 350 hours. Although any positive swell index indicates some waterproofing ability, a swell index of greater than about 50 indicates noteable waterproofing properties.

DESCRIPTION OF THE PREFERRED EMBODIMENTS

The following examples illustrate the invention without limitation. All parts and percentages are given by weight unless otherwise indicated.

Quaternary compounds are quantified by two phase titration with sodium laurylsulfate and an indicator. The mixture is buffered to a pH of 10.

Swell index is calculated as $$\left( \frac{\text{(Swell of Control - Swell of Sample)}}{\text{Swell of Control}} \right) \times 100$$

Procedure A—Didecyldimethylammonium hydroxide (Stoichiometric Amount of Metal Hydroxide)

180 grams (0.4 moles) of 80% didecyldimethylammonium chloride in 20% ethanol water (144 grams of DDAC), 180 ml of absolute denatured ethanol (denatured with methanol/isopropanol), and 26 grams (0.4 mole) of 85% potassium hydroxide pellets (22.1 grams of KOH) are mixed in a flask that is purged with nitrogen and equipped with a heating mantle and a magnetic stirrer. The mixture is stirred and heated at 60°–70° C. for three hours. The mixture is then allowed to cool to room temperature and finally cooled to 0° C. for at least one hour.

Potassium chloride precipitates, and the precipitate is collected on a vacuum filter. The solid is washed with cold ethanol and subsequently is dried, yielding 30 grams of dry potassium chloride. The quat solution is concentrated in a vacuum to about 75% active bases.

Yield is 180 grams of product containing 138 grams of didecyldimethylammonium hydroxide.

Procedure B—Didecyldimethylammonium hydroxide (Stoichiometric Excess of Metal Hydroxide)

A nitrogen purged reactor equipped with a heating mantle and a magnetic stir bar is charged with 0.4 mole of 80% didecyldimethylammonium chloride (144 grams of DDAC) in 20% ethanol/water, 180 ml of ethanol, and 0.49 mole of 85% potassium hydroxide (27.5 grams of KOH) pellets. The mixture is heated at 60°–70° C. for 3 hours, allowed to cool to room temperature, and then cooled to 0° C. for about one hour to precipitate potassium chloride. The precipitate is collected on a vacuum filter, and the solid is washed with cold ethanol. Potassium chloride yield is 30.8 grams.

The supernatant solution, which contained the hydroxy quat and 0.09 moles of excess potassium hydroxide, is stirred with 2 grams (0.045 moles) of carbon dioxide gas (from dry ice). The mixture is kept cold for an hour and then is vacuum filtered to remove 7.2 grams (theoretical 6.2 grams) of potassium carbonate.

Conversion percentage to the hydroxy quat is determined to be 99%.

Procedure C—Didecyldimethylammonium carbonate 180 grams (0.4 moles) of 80% didecyldimethylammonium chloride in 20% ethanol water (144 grams DDAC), 180 ml of absolute denatured ethanol (denatured with methanol/isopropanol), and 32 grams (0.49 mole) of 85% potassium hydroxide pellets (27 grams KOH) are mixed in a flask that is purged with nitrogen and equipped with a heating mantle and a magnetic stirrer. The mixture is stirred and heated at 60°–70° C. for three hours. The mixture is then allowed to cool to room temperature and finally cooled to 5° C. Potassium chloride precipitates, and the precipitate is collected on a vacuum filter. The solid is washed with cold ethanol and subsequently is dried, yielding 31 grams (calculated yield 29.6 grams) of dry potassium chloride.

The ethanolic solution of the hydroxy quat containing about 0.09 mole of unreacted KOH, is stirred while 50 grams of carbon dioxide (from sublimed carbon dioxide) are bubbled over one half hour. The resultant mixture is then filtered to remove 7.2 grams of potassium carbonate (6.2 grams calculated), and the filtrate is concentrated to yield an orange/brown liquid with 80–85% carbonate quat in water/ethanol and less than 0.1% chloride quat having a product with 98 to 99% exchanged quat purity.

Procedure D—Didecyldimethylammonium acetate 180 grams (0.4 mole) of 80% didecyldimethylammonium chloride in 20% ethanol water (144 grams of DDAC), 180 ml of absolute denatured ethanol (denatured with methanol/isopropanol), and 32 grams (0.49 mole) of 85% potassium hydroxide pellets (27 grams of KOH) are mixed in a flask that is purged with nitrogen and equipped with a heating mantle and a magnetic stirrer. The mixture is stirred and heated at 60°–70° C. for three hours. The mixture is then allowed to cool to room temperature and finally cooled to 5° C.

Potassium chloride precipitates, and the precipitate is collected on a vacuum filter. The solid is washed with cold ethanol and subsequently is dried, yielding 31 grams (calculated yield 29.6 grams) of dry potassium chloride.

The ethanolic solution of the hydroxy quat containing about 0.09 mole of unreacted KOH, is stirred while 50 grams of carbon dioxide (from sublimed carbon dioxide) are bubbled over one half hour. The resultant mixture is then filtered to remove 7.2 grams of potassium carbonate (6.2 grams calculated), and the filtrate is concentrated to yield an orange/brown liquid with 80–85% carbonate quat (0.4 mole of carbonate quat) and less than 0.1% chloride for a product with 98 to 99% exchanged quat purity.

The cold product, after filtration, is placed in a closed flask equipped with a condenser, addition funnel, and a tube connected to a water displacement type gas measuring device. An equivalent (0.4 mole), of acetic acid is added to the carbonate quat over five minutes. Immediate gas evolution is noted, and 5.75 liters of gas are collected over 15 minutes. The solvent is removed on a rotary evaporator after the carbon dioxide evolution ceased, and yields a yellow/orange liquid.

Quat analysis reveals that the product contains 85% active quat with 0.09% free chloride and 99% exchange.

Procedure E—Didecyldimethylanmmonium acetate (Direct Synthesis)

180 grams (0.4 mole) of 80% didecyldimethylammonium chloride in 20% ethanol water (144 grams of DDAC), 180 ml of anhydrous ethanol, a stoichiometric excess, and 47 grams (0.48 mole), of anhydrous potassium acetate is mixed in a flask that is purged with nitrogen and equipped with a heating mantle, a magnetic stirrer, and a condenser. The mixture is stirred and heated at 60°–70° C. for two hours. The insoluble potassium acetate crystals slowly dissolve, and a finer solid (KCl) separates. The mixture is then cooled to 0° C. and vacuum filtered, and the solid is washed with cold ethanol to remove 30.7 grams potassium chloride (theoretical 29.6 grams). The solution is concentrated, cooled, and filtered to remove 6.5 grams of potassium acetate (theoretical 7.8 grams).

Procedure F—Didecyldimethylammonium acetate (Hydroxy Quat/acid Synthesis)

180 grams (0.4 mole) of 80% didecyldimethylammonium chloride in 20% ethanol water (144 grams of DDAC), 180 ml of absolute denatured ethanol (denatured with methanol/isopropanyl), and 26 grams (0.4 mole) of 85% potassium hydroxide pellets (22 grams of KOH) are mixed in a flask that is purged with nitrogen and equipped with a heating mantle and a magnetic stirrer. The mixture is stirred and heated at 60°–70° C. for three hours. The mixture is then allowed to cool to room temperature and finally cooled to 0° C. for at least one hour.

Potassium chloride precipitates, and the precipitate is collected on a vacuum filter. The solid is washed with cold ethanol and subsequently is dried, yielding 30 grams of dry potassium chloride.

The hydroxy quat/ethanol solution is mixed with a stoichiometric amount of acetic acid to yield didecyldimethylammonium acetate.

Procedure G—Didecyldimethylammonium mixed coconut fatty acid carboxylate

The procedure of Procedure D is followed substituting 0.4 mole of mixed coconut fatty acid for the acetic acid to yield didecyldimethylammonium mixed coconut fatty acid carboxylate.

EXAMPLE 1—Didecyldimethylammonium Chloride (DDAC)/Polypropylene Glycol Monostearate (PGMS)/Water 3 parts of didecyldimethylammonium chloride and 2.5 parts of PGMS are melted together and stirred while 94.5 parts of warm (40° C.) water are added to yield a stable emulsion which is suitable for waterproofing and preserving wood.

EXAMPLE 2—DDAC/3% PGMS/Mineral Spirits

The method of Example 1 is followed substituting 3 parts of PGMS for the PGMS and 84 parts of mineral spirits for the water.

EXAMPLE 3—DDAC/6% PGMS/Mineral Spirits

The method of Example 2 is followed substituting 6 parts of PGMS for the PGMS and 91 parts of mineral spirits for the mineral spirits.

EXAMPLE 4—DDAC/8% PGMS/Mineral Spirits

The method of Example 2 is followed substituting 8 parts of PMGS for the PGMS and 89 parts of mineral spirits for the mineral spirits.

EXAMPLE 5—DDAC/12% PGMS/Mineral Spirits

The method of Example 2 is followed substituting 12 parts of PGMS for the PGMS and 85 parts of mineral spirits for the mineral spirits.

EXAMPLE 6—DDAC/9% Ethylene Glycol Monostearate (EGMS)/Water

The method of Example 1 is followed substituting 9 parts of EGMS for the PGMS and 88 parts of water for the water.

EXAMPLE 7—DDAC/10% Ethylene Glycol Distearate (EGDS)/Water

The method of Example 6 is followed substituting 10 parts of EGDS for the EGMS and 87 parts of water for the water.

EXAMPLE 8—DDAC/9% Sorbitan Tristearate (STS)/Water

The method of Example 1 is followed substituting 9 parts of STS for the PGMS and 88 parts of water for water.

EXAMPLE 9—DDAC/9% Sorbitan Monostearate (SMS)/Water

The method of Example 8 is followed substituting 9 parts of SMS for the STS.

EXAMPLE 10—DDAC/9% Polyethylene Glycol Distearate (PEG 400-DS)/Water

The method of Example 8 is followed substituting 9 parts of PEG 400-DS for the SMS.

EXAMPLE 11—DDAC/9% PEG 400-DS/Mineral Spirits

The method of Example 10 is followed substituting 88 parts of mineral spirits for the water.

EXAMPLE 12—Didecyldimethylammonium Hydroxide/PGMS/Water

The method of Example 1 is followed substituting 3 parts of didecyldimethylammonium hydroxide prepared by the method of Procedure A for the didecyldimethylammonium chloride.

EXAMPLE 13—Didecyldimethylammonium Carbonate/2.56 PGMS/Water

The method of Example 1 is followed substituting 3 parts of didecyldimethylammonium carbonate prepared by the method of Procedure C for the didecyldimethylammonium chloride.

EXAMPLE 14—Didecyldimethylammonium Carbonate/2.5% Glycerol Monolaureate (GML)/Water The method of Example 15 is followed substituting 2.5 parts of GML for the PGMS.

EXAMPLE 15—Didecyldimethylammonium Carbonate/2.5% Glycerol Monostearate (GMS)/Water The method of Example 14 is followed substituting 2.5 parts of GMS for the GML.

EXAMPLE 16—Didecyldimethylammonium Acetate/PGMS/Water

The method of Example 1 is followed substituting 3 parts of didecyldimethylammonium acetate prepared by the method of Procedure D for the didecyldimethylanmonium chloride.

EXAMPLE 17—Didecyldimethylammonium Mixed Coconut Fatty Acid Carboxylate/PGMS/Water The method of Example 1 is followed substituting 5 parts of didecyldimethylammonium mixed coconut fatty acid carboxylate prepared by the method of Procedure G for the didecyldimethylammonium chloride, 5 parts of PGMS for the PGMS, and 90 parts of water for the water.

EXAMPLE 18—Didecyldimethylammonium Chloride/PGMS/Water

End grain pine wafers are weighed and then soaked with a waterproofer, wood preservative system prepared according to the method of Example 1 until the samples are saturated with the treating mixture. The samples are then air dried to constant weight to determine the uptake of the waterproofer, wood preservative system.

The treated wafers are removed, dried to constant weight, and weighed periodically to determine resistance to leaching.

The dried treated wafers are soaked in water for 30 minutes to determine swelling. Swell is measured as the increase in length of the sample compared to an untreated control, and the swell index for each is calculated.

Results are illustrated in Table 1 and FIGS. 1A and 1B.

COMPARATIVE EXAMPLE 18A—Didecyldimethylammonium Chloride

The method of Example 18 is followed substituting didecyldimethylammonium chloride for the waterproofer, wood preservative system.

Results are illustrated in Table 1 and FIGS. 1A and 1B.

EXAMPLE 19—DDAC/3% PGMS/Mineral Spirits

The method of Example 18 is followed substituting a waterproofer, wood preservative system prepared according to the method of Example 2 for the waterproofer, wood preservative system.

Results are illustrated in Table 1.

EXAMPLE 20—DDAC/6% PGMS/Mineral Spirits

The method of Example 18 is followed substituting a waterproofer, wood preservative system prepared according to the method of Example 3 for the waterproofer, wood preservative system.

Results are illustrated in Table 1.

EXAMPLE 21—DDAC/8% PGMS/Mineral Spirits

The method of Example 18 is followed substituting a waterproofer, wood preservative system prepared according to the method of Example 4 for the waterproofer, wood preservative system.

Results are illustrated in Table 1.

EXAMPLE 22—DDAC/12% PGMS/Mineral Spirits

The method of Example 18 is followed substituting a waterproofer, wood preservative system prepared according to the method of Example 5 for the waterproofer, wood preservative system.

Results are illustrated in Table 1.

EXAMPLE 23—DDAC/9% EGMS/Water

The method of Example 18 is followed substituting a waterproofer, wood preservative system prepared according to the method of Example 6 for the waterproofer, wood preservative system.

Results are illustrated in Table 1.

EXAMPLE 24—DDAC/10% EGDS/Water

The method of Example 18 is followed substituting a waterproofer, wood preservative system prepared according to the method of Example 7 for the waterproofer, wood preservative system.

Results are illustrated in Table 1.

EXAMPLE 25—DDAC/9% STS/Water

The method of Example 18 is followed substituting a waterproofer, wood preservative system prepared according to the method of Example 8 for the waterproofer, wood preservative system.

Results are illustrated in Table 1.

EXAMPLE 26—DDAC/9% SMS/Water

The method of Example 18 is followed substituting a waterproofer, wood preservative system prepared according to the method of Example 9 for the waterproofer, wood preservative system.

Results are illustrated in Table 1.

EXAMPLE 27—DDAC/9% PEG 400-DS/Water

The method of Example 18 is followed substituting a waterproofer, wood preservative system prepared according to the method of Example 10 for the waterproofer, wood preservative system.

Results are illustrated in Table 1.

EXAMPLE 28—DDAC/9% PEG 400-DS/Mineral Spirits

The method of Example 18 is followed substituting a waterproofer, wood preservative system prepared according to the method of Example 11 for the waterproofer, wood preservative system.

Results are illustrated in Table 1.

EXAMPLE 29—Didecyldimethylammonium Hydroxide/PGMS/Water

The method of Example 18 is followed substituting a waterproofer, wood preservative system prepared according to the method of Example 12 for the waterproofer, wood preservative system.

Results are illustrated in Table 1 and FIGS. 1A and 1B.

COMPARATIVE EXAMPLE 29A—Didecyldimethylammonium Hydroxide

The method of Comparative Example 18A is followed substituting didecyldimethylammonium hydroxide for the didecyldimethylammonium chloride.

Results are illustrated in Table 1 and FIGS. 1A and 1B.

EXAMPLE 30—Didecyldimethylammonium Carbonate/2.5% PGMS/Water

The method of Example 18 is followed, substituting a waterproofer, wood preservative system prepared according to the method of Example 13 for the waterproofer, wood preservative system.

Results are illustrated in Table 1 and FIGS. 1A and 1B.

COMPARATIVE EXAMPLE 30A—Didecyldimethylammonium Carbonate

The method of Comparative Example 18A is followed substituting didecyldimethylammonium carbonate for the didecyldimethylammonium chloride to yield a clear solution.

Results are illustrated in Table 1 and FIGS. 1A and 1B.

EXAMPLE 31—Didecyldimethylammonium Carbonate/2.50 GML/Water

The method of Example 30 is followed substituting 2.5 parts of GML for the PGMS.

Results are illustrated in Table 1.

EXAMPLE 32—Didecyldimethylammonium Carbonate/2.5% GMS/Water

The method of Example 30 is followed substituting 2.5 parts of GMS for the PGMS.

Results are illustrated in Table 1.

EXAMPLE 33—Didecyldimethylammonium Acetate/PGMS/Water

The method of Example 18 is followed, substituting a waterproofer, wood preservative system prepared according to the method of Example 16, for the waterproofer, wood preservative system.

Results are illustrated in Table 1 and FIGS. 1A and 1B.

COMPARATIVE EXAMPLE 33A—Didecyldimethylammonium Acetate

The method of Comparative Example 18A is followed substituting didecyldimethylammonium acetate for the didecyldimethylammonium chloride.

Results are illustrated in FIGS. 1A and 1B.

EXAMPLE 34—Didecyldimethylammonium Mixed Coconut Fatty Acid Carboxylate/PGMS/Water The method of Example 18 is followed substituting a waterproofer, wood preservation system prepared according to the method of Example 17 for the waterproofer, wood preservative system to yield an emulsion.

Results are illustrated in Table 1.

COMPARATIVE EXAMPLE 34A—Didecyldimethylammonium Mixed Coconut Fatty Acid Carboxylate The method of Comparative Example 18A is followed substituting 5 parts of didecyldimethylammonium mixed coconut fatty acid carboxylate and 95 parts of water for the waterproofer, wood preservative system.

Results are illustrated in Table 1.

EXAMPLE 35—PGMS

The method of Example 18 is followed substituting a solution of 8 parts of PGMS and 92 parts of water for the waterproofer, wood preservative system.

Results are illustrated in Table 1.

COMPARATIVE EXAMPLE 35A—Mineral Spirits

The method of Example 18 is followed substituting a commercially available wax based biocide/mineral spirit based solution (Woodtreat MB*—KopCoat, Inc.)for the waterproofer, wood preservative system.

Results are illustrated in Table 1.

Table 1 illustrates the enhanced properties of waterproofer, wood preservative systems of the present invention.

TABLE 1

Properties of Waterproofer, Wood Preservative Systems

| Example | 18 | 18A | 19 | 20 | 21 | 22 | 23 | 24 | 25 | 26 | 27 | 28 |
|---|---|---|---|---|---|---|---|---|---|---|---|---|
| Composition | | | | | | | | | | | | |
| Quat | | | | | | | | | | | | |
| Chloride | 3 | 100 | 3 | 3 | 3 | 3 | 3 | 3 | 3 | 3 | 3 | 3 |
| Hydroxy | — | — | — | — | — | — | — | — | — | — | — | — |
| Carbonate | — | — | — | — | — | — | — | — | — | — | — | — |
| Acetate | — | — | — | — | — | — | — | — | — | — | — | — |
| Mixed Coconut Fatty Acid Carboxylate | — | — | — | — | — | — | — | — | — | — | — | — |
| Waterproofer | | | | | | | | | | | | |
| PGMS | 2.5 | — | 3 | 6 | 8 | 12 | — | — | — | — | — | — |
| EGMS | — | — | — | — | — | — | 9 | — | — | — | — | — |
| EGDS | — | — | — | — | — | — | — | 10 | — | — | — | — |
| STS | — | — | — | — | — | — | — | — | 9 | — | — | — |
| SMS | — | — | — | — | — | — | — | — | — | 9 | — | — |
| PEG 400-DS | — | — | — | — | — | — | — | — | — | — | 9 | 9 |
| GML | — | — | — | — | — | — | — | — | — | — | — | — |
| GMS | — | — | — | — | — | — | — | — | — | — | — | — |
| Wax-Based in Mineral Spirits Solvent | — | — | — | — | — | — | — | — | — | — | — | — |
| Water | 94.5 | — | — | — | — | — | 88 | 87 | 88 | 88 | 88 | — |
| Mineral Spirits | — | — | 94 | 91 | 89 | 85 | — | — | — | — | — | 88 |
| Properties | | | | | | | | | | | | |
| Swell Index (%) | 57 | — | 55 | 33 | 50 | 55 | 36 | 30 | 9 | 64 | — | — |
| Total Add On (%) | 5.4 | 35 | — | — | — | — | — | — | — | — | — | — |
| Solids or Add On Retained at 24 Hours Leaching, at Room Temperature (%) | — | — | — | — | — | — | — | — | — | — | — | — |
| Solids or Add On Retained at 300 Hours Leaching, at Room Temperature (%) | 3.2 | 0 | — | — | — | — | — | — | — | — | — | — |

| Example | 29 | 29A | 30 | 30A | 31 | 32 | 33 | 33A | 34 | 34A | 35 | 35A |
|---|---|---|---|---|---|---|---|---|---|---|---|---|
| Composition | | | | | | | | | | | | |
| Quat | | | | | | | | | | | | |
| Chloride | — | — | — | — | — | — | — | — | — | — | — | — |
| Hydroxy | 3 | 100 | — | — | — | — | — | — | — | — | — | — |
| Carbonate | — | — | 3 | 100 | 3 | - 3 | — | — | — | — | — | — |
| Acetate | — | — | — | — | — | — | 3 | 100 | — | — | — | — |
| Mixed Coconut Fatty Acid Carboxylate | — | — | — | — | — | — | — | — | 5 | 5 | — | — |
| Waterproofer | | | | | | | | | | | | |
| PGMS | 2.5 | — | 2.5 | — | — | — | 2.5 | — | 5 | — | 8 | — |
| EGMS | — | — | — | — | — | — | — | — | — | — | — | — |
| EGDS | — | — | — | — | — | — | — | — | — | — | — | — |
| STS | — | — | — | — | — | — | — | — | — | — | — | — |
| SMS | — | — | — | — | — | — | — | — | — | — | — | — |
| PEG 400-DS | — | — | — | — | — | — | — | — | — | — | — | — |
| GML | — | — | — | — | 2.5 | — | — | — | — | — | — | — |
| GMS | — | — | — | — | — | 2.5 | — | — | — | — | — | — |
| Wax-Based in Mineral Spirits Solvent | — | — | — | — | — | — | — | — | — | — | — | 1–2 |

TABLE 1-continued

Properties of Waterproofer, Wood Preservative Systems

| | | | | | | | | | | | | |
|---|---|---|---|---|---|---|---|---|---|---|---|---|
| Water | 94.5 | — | 94.5 | — | 94.5 | 94.5 | 94.5 | — | 90 | 95 | 92 | — |
| Mineral Spirits | — | — | — | — | — | — | — | — | — | — | — | 98–99 |
| Properties | | | | | | | | | | | | |
| Swell Index (%) | 14 | — | 71 | — | 14 | 57 | 57 | — | 50 | 14 | 0 | 43 |
| Total Add On (%) | 4.8 | 35 | 5.1 | 37 | 4.2 | 5.1 | 4.5 | 45 | 10 | 2.7 | 3.4 | 3.4 |
| Solids or Add On Retained at 24 Hours Leaching, at Room Temperature (%) | — | — | — | — | — | — | — | 103 | 103 | 100+ | 100+ | — |
| Solids or Add On Retained at 300 Hours Leaching, at Room Temperature (%) | 3.5 | 0 | 4.5 | 0 | 2.1 | 3.4 | 3 | 0 | — | — | — | — |

All patents, applications, articles, publications, and test methods mentioned herein are hereby incorporated by reference.

Many variations of the present invention will suggest themselves to those skilled in the art in light of the above detailed description. Such obvious variations are within the full intended scope of the appended claims.

I claim:

1. A metal-free, penetrating waterproofer, wood preservative system comprising:
   (A) a waterproofing and compatibility enhancing amount of one or more waterproofer compositions having the formula

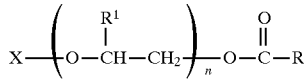

wherein:
   X is hydrogen or

R and $R^2$ independently are a $C_9$–$C_{50}$ group, saturated or unsaturated, optionally substituted with one or more saturated or unsaturated carbon groups, or one or more sulfate groups, uninterrupted or interrupted by one or more oxygen or boron atoms;
   $R^1$ is hydrogen or a methyl group; and n is an integer from 1 to 10;
   (B) a biocidal effective amount of at least one di $C_8$–$C_{12}$ alkyl or aryl-substituted $C_8$–$C_{12}$ alkyl, dimethyl quaternary ammonium composition and
   (C) a solvent.

2. A metal-free, penetrating waterproofer, wood preservation system as defined in claim 1 wherein said quaternary ammonium composition is selected from the group consisting of quaternary ammonium chlorides, quaternary ammonium hydroxides, quaternary ammonium carbonates, quaternary ammonium carboxylates, quaternary ammonium borates, and any combinations thereof.

3. A waterproofer, wood preservative system as defined in claim 1, wherein said waterproofer composition is component (A) wherein X is hydrogen, R is a $C_{17}$ alkyl group, $R^1$ is a methyl group, and n is 8.

4. A waterproofer, wood preservative system as defined in claim 1, wherein said waterproofer composition is component (A) wherein X is

and $R^2$ each are a $C_{17}$ alkyl group, $R^1$ is a hydrogen, and n is 1.

5. A metal-free, penetrating waterproofer, wood preservative system as defined in claim 1, wherein said quaternary ammonium composition comprises a di $C_8$–$C_{12}$ alkyl or aryl-substituted $C_8$–$C_{12}$ alkyl di methyl quaternary ammonium hydroxide.

6. A metal-free, penetrating waterproofer, wood preservative system as defined in claim 5, wherein said $C_8$–$C_{12}$ alkyl or aryl-substituted $C_8$–$C_{12}$ alkyl is selected from the group consisting of a $C_8$ alkyl, $C_9$ isoalkyl, $C_{10}$ alkyl, and $C_{12}$ alkyl group.

7. A metal-free, penetrating waterproofer, wood preservative system as defined in claim 5, wherein said quaternary ammonium composition comprises a di $C_8$–$C_{12}$ alkyl ammonium hydroxide.

8. A metal-free, penetrating waterproofer, wood preservative system as defined in claim 7, wherein said quaternary ammonium hydroxide is didecyldimethylammonium hydroxide.

9. A metal-free, penetrating waterproofer, wood preservative system as defined in claim 1, wherein said quaternary ammonium composition comprises a quaternary ammonium carbonate.

10. A waterproofer, wood preservative system as defined in claim 9, wherein said quaternary ammonium composition comprises a $C_8$–$C_{12}$ alkyl or aryl-substituted, $C_8$–$C_{12}$ alkyl quaternary ammonium carbonate having the formula

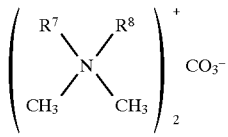

wherein $R^7$ is a $C_8$–$C_{12}$ alkyl or aryl-substituted $C_8$–$C_{12}$ alkyl group, and $R^8$ is a $C_8$–$C_{12}$ alkyl group.

11. A metal-free, penetrating waterproofer, wood preservative system as defined in claim 10, wherein said $C_8$–$C_{12}$ alkyl or aryl-substituted $C_8$–$C_{12}$ alkyl group is selected from the group consisting of a $C_8$ alkyl, $C_9$ isoalkyl, $C_{10}$ alkyl, and $C_{12}$ alkyl group.

12. A metal-free, penetrating waterproofer, wood preservative system as defined in claim 9, wherein said quaternary ammonium carbonate is a di $C_8$–$C_{12}$ alkyl ammonium carbonate having the formula

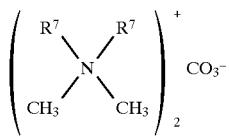

wherein $R^7$ is a $C_8$–$C_{12}$ alkyl group.

13. A metal-free, penetrating waterproofer, wood preservative system as defined in claim 12, wherein said di-$C_8$–$C_{12}$ alkyl quaternary ammonium carbonate is didecyidimethylammonium carbonate.

14. A metal-free, penetrating waterproofer, wood preservative system as defined in claim 9, wherein said quaternary ammonium carbonate comprises (a) at least one di $C_8$–$C_{12}$ alkyl quaternary ammonium carbonate having the formula

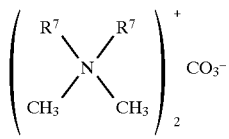

wherein $R^7$ is a $C_8$–$C_{12}$ alkyl group; and (b)(1) at least one di $C_8$–$C_{12}$ alkyl quaternary ammonium bicarbonate having the formula

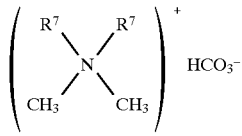

wherein $R^7$ is the same or a different $C_8$–$C_{12}$ alkyl group as in (a), or (b)(2) at least one di $C_8$–$C_{12}$ alkyl quaternary ammonium metal carbonate having the formula

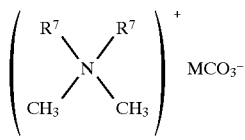

wherein $R^7$ is the same or a different $C_8$–$C_{12}$ alkyl group as in (a) or (b) and M is a non-coupler metal, or (b)(3) a combination of (b)(1) and (b)(2).

15. A metal-free, penetrating waterproofer, wood preservative system as defined in claim 1, wherein said quaternary ammonium composition comprises a quaternary ammonium carboxylate.

16. A waterproofer, wood preservative system as defined in claim 15, wherein said quaternary ammonium composition comprises a quaternary ammonium carboxylate having the formula

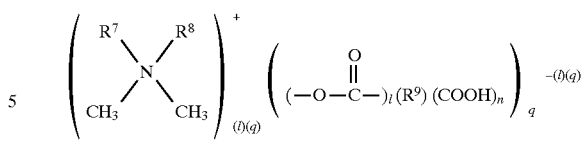

wherein $R^7$ is a $C_8$–$C_{12}$ alkyl or aryl-substituted $C_8$–$C_{12}$ alkyl group; $R^8$ is a $C_8$–$C_{12}$ alkyl group; $R^9$ is a $C_1$–$C_{100}$ group, optionally substituted with one or more sulfate groups, interrupted or uninterrupted by one or more oxygen or boron atoms; l and q independently are 1, 2, and 3 and (l)(q) is 1, 2, or 3; and r is 0 or an integer from 1 to 50.

17. A metal-free, penetrating waterproofer, wood preservative system as defined in claim 16, wherein said $C_8$–$C_{12}$ alkyl group is selected from the group consisting of a $C_8$ alkyl, $C_9$ isoalkyl, $C_{10}$ alkyl, and $C_{12}$ alkyl group.

18. A metal-free, penetrating waterproofer, wood preservative system as defined in claim 16, wherein said quaternary ammonium carboxylate comprises a composition having the formula

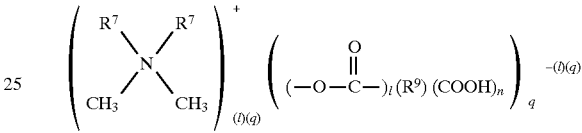

wherein $R^7$ is a $C_8$–$C_{12}$ alkyl group; $R^9$ is a $C_1$–$C_{100}$ group, optionally substituted by one or more sulfate groups, uninterrupted or interrupted by one or more oxygen or boron atoms; l and q independently are 1, 2, or 3 and (l)(q) is 1, 2, or 3; and r is 0 or an integer from 1 to 50.

19. A metal-free, penetrating waterproofer, wood preservative system as defined in claim 18, wherein said quaternary ammonium carboxylate is didecyidimethylammonium carboxylate.

20. A metal-free, penetrating waterproofer, wood preservative system as defined in claim 1, wherein said quaternary ammonium composition comprises a quaternary ammonium borate.

21. A metal-free, penetrating waterproofer, wood preservative system as defined in claim 20, wherein said quaternary ammonium composition is a quaternary ammonium borate having the formula

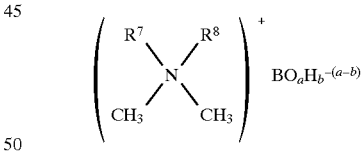

wherein $R^7$ is a $C_8$–$C_{12}$ alkyl or aryl-substituted $C_8$–$C_{12}$ alkyl group; $R^8$ is a $C_8$–$C_{12}$ alkyl group; a is 2 or 3, but when a is 2, b is 0 or 1 and when a is 3, b is 0, 1, or 2.

22. A metal-free, penetrating waterproofer, wood preservative system as defined in claim 20, wherein said $C_8$–$C_{12}$ alkyl group is selected from the group consisting of a $C_8$ alkyl, $C_9$ isoalkyl, $C_{10}$ alkyl, and $C_{12}$ alkyl group.

23. A metal-free, penetrating waterproofer, wood preservative system as defined in claim 22, wherein said quaternary borate is didecyldimethylammonium borate.

24. A metal-free, penetrating waterproofer, wood preservative system as defined in claim 1, wherein said solvent comprises an aqueous solvent.

25. A metal-free, penetrating waterproofer, wood preservative system as defined in claim 24, wherein said aqueous solvent is selected from the group consisting of water, aqueous ammonia, and aqueous acetic acid.

26. A metal-free, penetrating waterproofer, wood preservative system as defined in claim 1, wherein said solvent comprises an organic solvent.

27. A metal-free, penetrating waterproofer, wood preservative system as defined in claim 26, wherein said solvent comprises mineral spirits.

28. A metal-free, penetrating waterproofer, wood preservative system as defined in claim 1, comprising from about 0.1 to about 10 parts by weight of quaternary ammonium composition, from about 0.1 to about 10 parts by weight of waterproofer composition, and from about 99.8 to about 80 parts by weight of solvent based upon 100 parts by weight of quaternary ammonium composition, waterproofing composition, and solvent combined.

29. A metal-free, penetrating waterproofer, wood preservative system as defined in claim 28, comprising from about 2 to about 6 parts by weight of quaternary ammonium composition, from about 2 to about 8.5 percent by weight of waterproofer composition, and from about 99.8 to about 85.5 parts by weight of solvent based upon 100 parts by weight of quaternary ammonium composition, waterproofing composition, and solvent combined.

30. A method for waterproofing, preserving, or waterproofing and preserving a wood substrate comprising treating said substrate with a metal-free, penetrating waterproofer, wood preservative system as defined in claim 1.

31. A metal-free, penetrating waterproofer, wood preservative system as defined in claim 5, wherein said quaternary ammonium hydroxide is prepared by reacting a di $C_8$–$C_{12}$ alkyl or aryl-substituted $C_8$–$C_{12}$ alkyl, dimethyl quaternary ammonium chloride reactant and a metal hydroxide reactant in a solvent comprising a $C_1$–$C_4$ normal alcohol, said metal hydroxide being present in an amount sufficient to yield said di $C_8$–$C_{12}$ alkyl or aryl-substituted $C_8$–$C_{12}$ alkyl, dimethyl quaternary ammonium hydroxide.

32. A metal-free, penetrating waterproofer, wood preservative system as defined in claim 9, wherein said quaternary ammonium carbonate is prepared by
  (a) reacting a di $C_8$–$C_{12}$ alkyl or aryl-substituted $C_8$–$C_{12}$ alkyl, dimethyl quaternary ammonium chloride reactant and a metal hydroxide reactant in a solvent comprising a $C_1$–$C_4$ normal alcohol, said metal hydroxide being present in an amount sufficient to yield a di $C_8$–$C_{12}$ alkyl or aryl-substituted $C_8$–$C_{12}$ alkyl, dimethyl quaternary ammonium hydroxide, a metal chloride and, optionally, unreacted metal hydroxide; and
  (b) reacting said di $C_8$–$C_{12}$ alkyl or aryl-substituted $C_8$–$C_{12}$ alkyl, dimethyl quaternary ammonium hydroxide and, optionally, any unreacted metal hydroxide with carbon dioxide to yield said di $C_8$–$C_{12}$ alkyl or aryl-substituted $C_8$–$C_{12}$ alkyl, dimethyl quaternary ammonium carbonate and, optionally, a metal carbonate.

33. A waterproofer, wood preservative system as defined in claim 15, wherein said quaternary ammonium carboxylate is prepared by
  (a) reacting a di $C_8$–$C_{12}$ alkyl or aryl-substituted $C_8$–$C_{12}$ alkyl, dimethyl alkyl quaternary ammonium chloride reactant and a metal hydroxide reactant in a solvent comprising a $C_1$–$C_4$ normal alcohol, said metal hydroxide being present in an amount sufficient to yield a di $C_8$–$C_{12}$ alkyl or aryl-substituted $C_8$–$C_{12}$ alkyl, dimethyl quaternary ammonium hydroxide, a metal chloride and, optionally, unreacted metal hydroxide;
  (b) reacting said di $C_8$–$C_{12}$ alkyl or aryl-substituted $C_8$–$C_{12}$ alkyl, dimethyl quaternary ammonium hydroxide and, optionally, any unreacted metal hydroxide with carbon dioxide to yield a di $C_8$–$C_{12}$ alkyl or aryl-substituted $C_8$–$C_{12}$ alkyl, dimethyl quaternary ammonium carbonate and, optionally, a metal carbonate;
  (c) reacting said di $C_8$–$C_{12}$ alkyl or aryl-substituted $C_8$–$C_{12}$ alkyl, dimethyl quaternary ammonium carbonate with at least one carboxylic acid having the formula

wherein $R^9$ is a optionally substituted, interrupted or uninterrupted $C_1$–$C_{100}$ group; l and q independently are 1, 2, or 3 and (l)(q) is 1, 2, or 3; and r is 0 or an integer from 1 to 50, to yield said di $C_8$–$C_{12}$ alkyl or aryl-substituted $C_8$–$C_{12}$ alkyl, dimethyl quaternary ammonium carboxylate.

34. A metal-free, penetrating waterproofer, wood preservative system as defined in claim 15, wherein said quaternary ammonium carboxylate is prepared by
  (a) reacting a di $C_8$–$C_{12}$ alkyl or aryl-substituted $C_8$–$C_{12}$ alkyl, dimethyl quaternary ammonium chloride reactant and at least one metal carboxylate having the formula

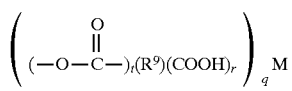

wherein $R^9$ is a optionally substituted, interrupted or uninterrupted $C_1$–$C_{20}$ group; M is a mono-, di- or tri-valent metal; l and q independently are 1, 2, 3; (l) (q) is 1, 2, or 3; and l is 1 if M is mono-valent, 2 if M is di-valent, or 3 if M is tri-valent; and r is 0 or an integer from 1 to 50, in a solvent comprising a $C_1$–$C_4$ normal alcohol, to yield said di $C_8$–$C_{12}$ alkyl or aryl substituted $C_8$–$C_{12}$ alkyl, dimethyl quaternary ammonium carboxylate.

35. A metal-free, penetrating waterproofer system as defined in claim 1 wherein said waterproofer composition comprises from about 0.1 to about 20 parts by weight and said solvent comprises from about 80 to about 99.9 percent by weight based upon 100 parts by weight of waterproofer composition and solvent combined.

36. A metal-free, penetrating waterproofer system as defined in claim 35 wherein said waterproofer composition comprises from about 0.2 to about 5 parts by weight and said solvent comprises from about 95 to about 99.8 percent by weight based upon 100 parts by weight of waterproofer composition and solvent combined.

37. A metal-free, penetrating waterproofer wood preservative system as defined in claim 1, wherein said waterproofer composition comprises from about 0.1 to about 15 parts by weight, said quaternary ammonium composition comprises from about 0.1 to about 10 parts by weight, and said solvent comprises from about 99.8 to about 75 parts by weight based upon 100 parts by weight of waterproofer composition, quaternary ammonium composition and solvent combined.

38. A metal-free, penetrating waterproofer wood preservative system as defined in claim 37, wherein said waterproofer composition comprises from about 0.5 to about 6 parts by weight, said quaternary ammonium composition comprises from about 0.5 to about 8.5 parts by weight, and said solvent comprises from about 96 to about 85.5 parts by weight based upon 100 parts by weight of waterproofer composition, quaternary ammonium composition and solvent combined.

39. A method of preparing a metal-free, penetrating waterproofer, wood preservative system comprising:

(A) melting a waterproofing and compatibility enhancing amount of
(i) a waterproofing composition having the formula

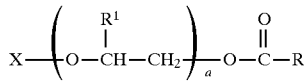

wherein:
X is hydrogen or

R and $R^2$ independently are a $C_9$–$C_{50}$ group, saturated or unsaturated, optionally substituted with one or more saturated or unsaturated carbon group, or one or more sulfate groups, interrupted or uninterrupted by one or more oxygen or boron atoms;
$R^1$ is hydrogen or a methyl group; and a is an integer from 1 to 10; and
(ii) a biocidal effective amount of a quaternary ammonium hydroxide prepared by reacting a $C_8$–$C_{12}$ alkyl or aryl-substituted $C_8$–$C_{12}$ alkyl, dimethyl quaternary ammonium chloride reactant and a metal hydroxide reactant in a solvent comprising a $C_1$–$C_4$ normal alcohol, said metal hydroxide being present in an amount sufficient to yield said alkyl or aryl-substituted $C_8$–$C_{12}$ alkyl, dimethyl quaternary ammonium hydroxide; and
(B) adding a solvent to the melt.

40. Water and biodegradation resistant wood comprising
(I) a substrate comprising wood, and
(II) a metal-free, penetrating wood-preservative comprising:
(A) a waterproofing and compatibility enhancing amount of
(i) a waterproofer composition having the formula

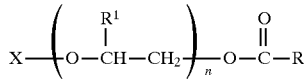

wherein:
X is hydrogen or

R and $R^2$ independently are a $C_9$–$C_{50}$ group, saturated or unsaturated, optionally substituted with one or more saturated or unsaturated carbon group, or one or more sulfate groups, uninterrupted or interrupted by one or more oxygen or boron atoms;
$R^1$ is hydrogen or a methyl group; and n is an integer from 1 to 10;
(ii) a waterproofer composition having the formula

wherein:
$R^6$ is a saturated or unsaturated $C_6$–$C_{30}$ group, optionally substituted with one or more saturated or unsaturated carbon group, one or more sulfate groups, or any combination thereof, uninterrupted or interrupted with one or more oxygen or boron atoms; and p is an integer from 1 to 30; or
(iii) a combination of any of (i) and (ii);
(B) a biocidal effective amount of at least one $C_1$–$C_{20}$ alkyl or aryl-substituted $C_1$–$C_{20}$ alkyl, $C_8$–$C_{20}$ alkyl quaternary ammonium composition; and
(C) a solvent.

41. Wood as defined in claim 40, wherein said quaternary ammonium composition is selected from the group consisting of quaternary ammonium chlorides, quaternary ammonium hydroxides, quaternary ammonium carbonates, quaternary ammonium carboxylates, quaternary ammonium borates, and any combinations thereof.

42. Wood as defined in claim 40, wherein said solvent comprises an aqueous solvent.

43. Wood as defined in claim 42, wherein said aqueous solvent is selected from the group consisting of water, aqueous ammonia, and aqueous acetic acid.

44. Water and biodegradation resistant wood comprising:
(I) a substrate comprising wood, and
(II) a metal-free penetrating waterproofer, wood preservative system comprising:
(A) a waterproofing and compatibility enhancing amount of
(i) a waterproofer composition having the formula

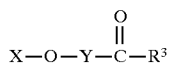

wherein:
X is hydrogen or

Y is any one of Y(l), Y(ii) or Y(iii) wherein Y(l) is

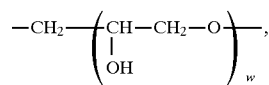

optionally substituted with one or more $C_1$–$C_9$ groups or one or more sulfate groups, interrupted or uninterrupted by one or more oxygen or boron atoms or any combination thereof, or Y(ii) is

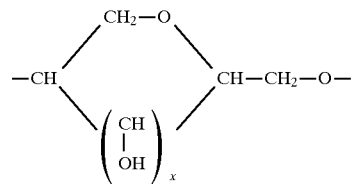

or an enantiomer thereof,
optionally substituted with one or more $C_1$–$C_9$ groups or one or more sulfate groups, interrupted or uninterrupted by one or more oxygen or boron atoms or any combination thereof, or Y(iii) is

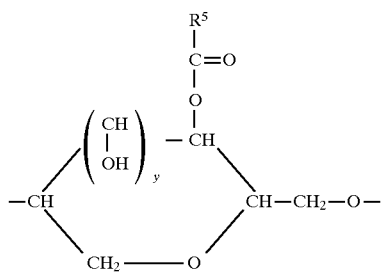

or an enantiomer thereof,
optionally substituted with one or more $C_1$–$C_9$ groups or one or more sulfate groups, interrupted or uninterrupted by one or more oxygen or boron atoms or any combination thereof wherein the number of carbons in Y ranges from 3–12;

$R^3$, $R^4$, and $R^5$ independently are a saturated or unsaturated $C_9$–$C_{50}$ group, optionally substituted with one or more saturated or unsaturated group, one or more oxygen or boron atoms or sulfate groups or a combination thereof, uninterrupted or interrupted with one or more oxygen or boron atoms;

w is an integer from 1 to 10; and
x and y are 0, 1, or 2;

(ii) a waterproofer composition having the formula

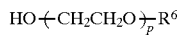

wherein:
$R^6$ is a saturated or unsaturated $C_6$–$C_{30}$ group, optionally substituted with one or more saturated or unsaturated carbon group, one or more sulfate groups or any combination thereof, uninterrupted or interrupted with one or more oxygen or boron atoms; and p is an integer from 1 to 30; or (iii) a combination of any of (i) and (ii);

(B) a biocidal effective amount of at least one $C_1$–$C_{20}$ alkyl or aryl-substituted $C_1$–$C_{20}$ alkyl, $C_8$–$C_{20}$ alkyl quaternary ammonium composition; and (C) a solvent.

45. Wood as defined in claim 44, wherein said quaternary ammonium composition is selected from the group consisting of quaternary ammonium chlorides, quaternary ammonium hydroxides, quaternary ammonium carbonates, quaternary ammonium carboxylates, quaternary ammonium borates, and any combination thereof.

46. Wood as defined in claim 44, wherein said solvent comprises an aqueous solvent.

47. Wood as defined in claim 46, wherein said aqueous solvent is selected from the group consisting of water, aqueous ammonia, and aqueous acetic acid.

48. A metal-free, penetrating waterproofer, wood preservative system comprising:

(A) a waterproofing and compatibility enhancing amount of one or more waterproofer compositions having the formula:

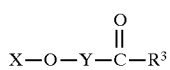

wherein:

X is hydrogen or

Y is selected from the group consisting of Y(l), Y(ii) and Y(iii) wherein Y(l) is

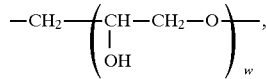

optionally substituted with one or more $C_1$–$C_9$ groups or one or more sulfate groups, interrupted or uninterrupted with one or more oxygen or boron atoms, or any combination thereof; Y(ii) is

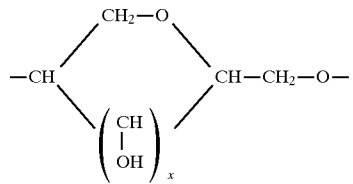

or an enantiomer thereof,
optionally substituted with one or more $C_1$–$C_9$ groups or one or more sulfate groups, interrupted or unterrupted by one or more oxygen or boron atoms, or any combination thereof; and wherein Y(iii) is

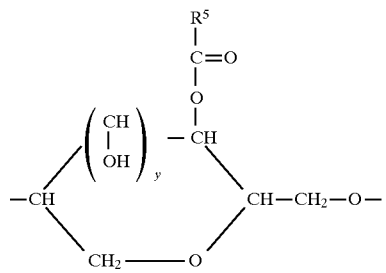

or an enantiomer thereof,
unsubstituted or substituted with one or more $C_1$–$C_9$ groups or one or more oxygen or boron atoms, sulfate groups, or any combination thereof wherein the number of carbons in Y ranges from 3–12;

$R^3$, $R^4$, and $R^5$ independently are a saturated or unsaturated $C_9$–$C_{50}$ group, optionally substituted with one or more saturated or unsaturated group, one or more sulfate groups or a combination thereof, uninterrupted or interrupted with one or more oxygen or boron atoms;

w is an integer from 1 to 10; and
x and y are 0, 1, or 2;

(B) a biocidal effective amount of at least one di $C_8$–$C_{12}$ alkyl or aryl-substituted $C_8$–$C_{12}$ alkyl, dimethyl quaternary ammonium composition; and (C) a solvent.

49. A waterproofer, wood preservative system as defined in claim 48 wherein X is hydrogen; $R^3$ is a $C_{17}$ alkyl group; and w is 1.

50. A waterproofer, wood preservative system as defined in claim 48 wherein X is hydrogen; $R^3$ is a $C_{11}$ alkyl group; and w is 1.

51. A waterproofer, wood preservative system as defined in claim 48 wherein: X is hydrogen;

Y is

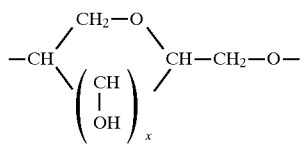

or an enantiomer thereof, $R^3$ is a $C_{17}$ alkyl group; and x is 0, 1, 2 or 4.

52. A waterproofer, wood preservative system as defined in claim 48 wherein:

X is

Y is

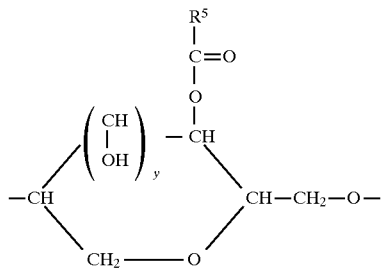

or an enantiomer thereof;

$R^3$, $R^4$, and $R^5$ each a $C_{17}$ alkyl group; and y is 1.

53. A metal-free, penetrating waterproofer, wood preservation system as defined in claim 48 wherein said quaternary ammonium composition is selected from the group consisting of quaternary ammonium chlorides, quaternary ammonium hydroxides, quaternary ammonium carbonates, quaternary ammonium carboxylates, quaternary ammonium borates, and any combinations thereof.

54. A metal-free, penetrating waterproofer, wood preservative system as defined in claim 48, wherein said quaternary ammonium composition comprises a di $C_8$–$C_{12}$ alkyl or aryl-substituted $C_8$–$C_{12}$ alkyl di methyl quaternary ammonium hydroxide.

55. A metal-free, penetrating waterproofer, wood preservative system as defined in claim 54, wherein said $C_8$–$C_{12}$ alkyl or aryl-substituted $C_8$–$C_{12}$ alkyl is selected from the group consisting of a $C_8$ alkyl, $C_9$ isoalkyl, $C_{10}$ alkyl, and $C_{12}$ alkyl group.

56. A metal-free, penetrating waterproofer, wood preservative system as defined in claim 54, wherein said quaternary ammonium composition comprises a di $C_8$–$C_{12}$ alkyl ammonium hydroxide.

57. A metal-free, penetrating waterproofer, wood preservative system as defined in claim 56, wherein said quaternary ammonium hydroxide is didecyldimethylammonium hydroxide.

58. A metal-free, penetrating waterproofer, wood preservative system as defined in claim 48, wherein said quaternary ammonium composition comprises a quaternary ammonium carbonate.

59. A waterproofer, wood preservative system as defined in claim 58, wherein said quaternary ammonium composition comprises a $C_8$–$C_{12}$ alkyl or aryl-substituted, $C_8$–$C_{12}$ alkyl quaternary ammonium carbonate having the formula

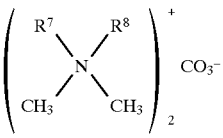

wherein $R^7$ is a $C_8$–$C_{12}$ alkyl or aryl-substituted $C_8$–$C_{12}$ alkyl group, and $R^8$ is a $C_8$–$C_{12}$ alkyl group.

60. A metal-free, penetrating waterproofer, wood preservative system as defined in claim 59, wherein said $C_8$–$C_{12}$ alkyl or aryl-substituted $C_8$–$C_{12}$ alkyl group is selected from the group consisting of a $C_8$ alkyl, $C_9$ isoalkyl, $C_{10}$ alkyl, and $C_{12}$ alkyl group.

61. A metal-free, penetrating waterproofer, wood preservative system as defined in claim 58, wherein said quaternary ammonium carbonate comprises a di $C_8$–$C_{12}$ alkyl ammonium carbonate having the formula

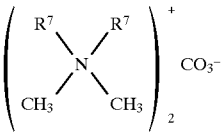

wherein $R^7$ is a $C_8$–$C_{12}$ alkyl group.

62. A metal-free, penetrating waterproofer, wood preservative system as defined in claim 61, wherein said di $C_8$–$C_{12}$ alkyl quaternary ammonium carbonate is didecyldimethylammonium carbonate.

63. A metal-free, penetrating waterproofer, wood preservative system as defined in claim 58, wherein said quaternary ammonium carbonate comprises (a) at least one di $C_8$–$C_{12}$ alkyl quaternary ammonium carbonate having the formula

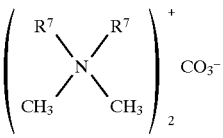

wherein $R^7$ is a $C_8$–$C_{12}$ alkyl group; and (b)(1) at least one di $C_8$–$C_{12}$ alkyl quaternary ammonium bicarbonate having the formula

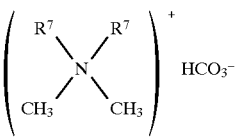

wherein $R^7$ is the same or a different $C_8$–$C_{12}$ alkyl group as in (a), or (b)(2) at least one di $C_8$–$C_{12}$ alkyl quaternary ammonium metal carbonate having the formula

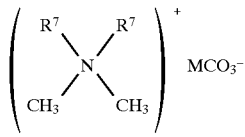 MCO$_3^-$ wherein R$^7$ is the same or a different C$_8$–C$_{12}$ alkyl group as in (a) or (b) and M is a non-coupler metal, or (b)(3) a combination of (b)(1) and (b)(2).

64. A metal-free, penetrating waterproofer, wood preservative system as defined in claim 48, wherein said quaternary ammonium composition comprises a quaternary ammonium carboxylate.

65. A waterproofer, wood preservative system as defined in claim 64, wherein said quaternary ammonium composition comprises a quaternary ammonium carboxylate having the formula

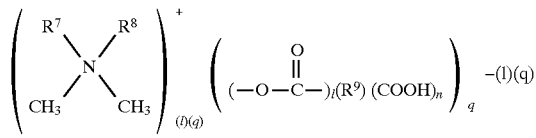

wherein R$^7$ is a C$_8$–C$_{12}$ alkyl or aryl-substituted C$_8$–C$_{12}$ alkyl group; R$^8$ is a C$_8$–C$_{12}$ alkyl group; R$^9$ is a C$_1$–C$_{100}$ group, optionally substituted with one or more sulfate groups, interrupted or uninterrupted by one or more oxygen or boron atoms; l and q independently are 1, 2, and 3 and (l)(q) is 1, 2, or 3; and r is 0 or an integer from 1 to 50.

66. A metal-free, penetrating waterproofer, wood preservative system as defined in claim 65, wherein said C$_8$–C$_{12}$ alkyl group is selected from the group consisting of a C$_8$ alkyl, C$_9$ isoalkyl, C$_{10}$ alkyl, and C$_{12}$ alkyl group.

67. A metal-free, penetrating waterproofer, wood preservative system as defined in claim 65, wherein said quaternary ammonium carboxylate comprises a composition having the formula

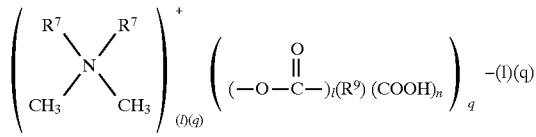

wherein R$^7$ is a C$_8$–C$_{12}$ alkyl group; R$^9$ is a C$_1$–C$_{100}$ group, optionally substituted by one or more sulfate groups, uninterrupted or interrupted by one or more oxygen or boron atoms; l and q independently are 1, 2, or 3 and (l) (q) is 1, 2, or 3; and r is 0 or an integer from 1 to 50.

68. A metal-free, penetrating waterproofer, wood preservative system as defined in claim 67, wherein said quaternary ammonium carboxylate is didecyldimethylammonium carboxylate.

69. A metal-free, penetrating waterproofer, wood preservative system as defined in claim 48, wherein said quaternary ammonium composition comprises a quaternary ammonium borate.

70. A metal-free, penetrating waterproofer, wood preservative system as defined in claim 69, wherein said quaternary ammonium composition comprises a quaternary ammonium borate having the formula

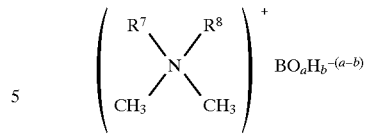 BO$_a$H$_b^{-(a-b)}$ wherein R$^7$ is a C$_8$–C$_{12}$ alkyl or aryl-substituted C$_8$–C$_{12}$ alkyl group; R$^8$ is a C$_8$–C$_{12}$ alkyl group; a is 2 or 3, but when a is 2, b is 0 or 1 and when a is 3, b is 0, 1, or 2.

71. A metal-free, penetrating waterproofer, wood preservative system as defined in claim 69, wherein said C$_8$–C$_{12}$ alkyl group is selected from the group consisting of a C$_8$ alkyl, C$_9$ isoalkyl, C$_{10}$ alkyl, and C$_{12}$ alkyl group.

72. A metal-free, penetrating waterproofer, wood preservative system as defined in claim 71, wherein said quaternary borate is didecyldimethylammonium borate.

73. A metal-free, penetrating waterproofer, wood preservative system as defined in claim 48, wherein said solvent comprises an aqueous solvent.

74. A metal-free, penetrating waterproofer, wood preservative system as defined in claim 73, wherein said aqueous solvent is selected from the group consisting of water, aqueous ammonia, and aqueous acetic acid.

75. A metal-free, penetrating waterproofer, wood preservative system as defined in claim 48 wherein said solvent comprises an organic solvent.

76. A metal-free, penetrating waterproofer, wood preservative system as defined in claim 75, wherein said solvent comprises mineral spirits.

77. A metal-free, penetrating waterproofer, wood preservative system as defined in claim 48, comprising from about 0.1 to about 10 parts by weight of quaternary ammonium composition, from about 0.1 to about 10 parts by weight of waterproofer composition, and from about 99.8 to about 80 parts by weight of solvent based upon 100 parts by weight of quaternary ammonium composition, waterproofing composition, and solvent combined.

78. A metal-free, penetrating waterproofer, wood preservative system as defined in claim 77, comprising from about 2 to about 6 parts by weight of quaternary ammonium composition, from about 2 to about 8.5 percent by weight of waterproofer composition, and from about 99.8 to about 85.5 parts by weight of solvent based upon 100 parts by weight of quaternary ammonium composition, waterproofing composition, and solvent combined.

79. A method for waterproofing, preserving, or waterproofing and preserving a wood substrate comprising treating said substrate with a metal-free, penetrating waterproofer, wood preservative system as defined in claim 48.

80. A metal-free, penetrating waterproofer, wood preservative system as defined in claim 54, wherein said quaternary ammonium hydroxide is prepared by reacting a di C$_8$–C$_{12}$ alkyl or aryl-substituted C$_8$–C$_{12}$ alkyl, dimethyl quaternary ammonium chloride reactant and a metal hydroxide reactant in a solvent comprising a C$_1$–C$_4$ normal alcohol, said metal hydroxide being present in an amount sufficient to yield said di C$_8$–C$_{12}$ alkyl or aryl-substituted C$_8$–C$_{12}$ alkyl, dimethyl quaternary ammonium hydroxide.

81. A metal-free, penetrating waterproofer, wood preservative system as defined in claim 58, wherein said quaternary ammonium carbonate is prepared by (a) reacting a di C$_8$–C$_{12}$ alkyl or aryl-substituted C$_8$–C$_{12}$ alkyl, dimethyl quaternary ammonium chloride reactant and a metal hydroxide reactant in a solvent comprising a C$_1$–C$_4$ normal alcohol, said metal hydroxide being present in an amount sufficient to yield a di $C_8$–$C_{12}$ alkyl or aryl-substituted $C_8$–$C_{12}$ alkyl, dimethyl quaternary ammonium hydroxide, a metal chloride and, optionally, unreacted metal hydroxide; and (b) reacting said di $C_8$–$C_{12}$ alkyl or aryl-substituted $C_8$–$C_{12}$ alkyl, dimethyl quaternary ammonium hydroxide and, optionally, any unreacted metal hydroxide with carbon dioxide to yield said di $C_8$–$C_{12}$ alkyl or aryl-substituted $C_8$–$C_{12}$ alkyl, dimethyl quaternary ammonium carbonate and, optionally, a metal carbonate.

82. A waterproofer, wood preservative system as defined in claim 69, wherein said quaternary ammonium carboxylate is prepared by (a) reacting a di $C_8$–$C_{12}$ alkyl or aryl-substituted $C_8$–$C_{12}$ alkyl, dimethyl alkyl quaternary ammonium chloride reactant and a metal hydroxide reactant in a solvent comprising a $C_1$–$C_4$ normal alcohol, said metal hydroxide being present in an amount sufficient to yield a di $C_8$–$C_{12}$ alkyl or aryl-substituted $C_8$–$C_{12}$ alkyl, dimethyl quaternary ammonium hydroxide, a metal chloride and, optionally, unreacted metal hydroxide;

(b) reacting said di $C_8$–$C_{12}$ alkyl or aryl-substituted $C_8$–$C_{12}$ alkyl, dimethyl quaternary ammonium hydroxide and, optionally, any unreacted metal hydroxide with carbon dioxide to yield a di $C_8$–$C_{12}$ alkyl or aryl-substituted $C_8$–$C_{12}$ alkyl, dimethyl quaternary ammonium carbonate and, optionally, a metal carbonate;

(c) reacting said di $C_8$–$C_{12}$ alkyl or aryl-substituted $C_8$–$C_{12}$ alkyl, dimethyl quaternary ammonium carbonate with at least one carboxylic acid having the formula

wherein $R^9$ is a optionally substituted, interrupted or uninterrupted $C_1$–$C_{100}$ group; l and q independently are 1, 2, or 3 and (l) (q) is 1, 2, or 3; and r is 0 or an integer from 1 to 50, to yield said di $C_8$–$C_{12}$ alkyl or aryl-substituted $C_8$–$C_{12}$ alkyl, dimethyl quaternary ammonium carboxylate.

83. A metal-free, penetrating waterproofer, wood preservative system as defined in claim 69, wherein said quaternary ammonium carboxylate is prepared by (a) reacting a di $C_8$–$C_{12}$ alkyl or aryl-substituted $C_8$–$C_{12}$ alkyl, dimethyl quaternary ammonium chloride reactant and at least one metal carboxylate having the formula

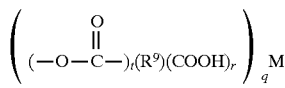

wherein $R^9$ is a optionally substituted, interrupted or uninterrupted $C_1$–$C_{20}$ group; M is a mono-, di- or tri-valent metal; f and q independently are 1, 2, 3; (l) (q) is 1, 2, or 3; and l is 1 if M is mono-valent, 2 if M is di-valent, or 3 if M is tri-valent; and r is 0 or an integer from 1 to 50, in a solvent comprising a $C_1$–$C_4$ normal alcohol, to yield said di $C_8$–$C_{12}$ alkyl or aryl substituted $C_8$–$C_{12}$ alkyl, dimethyl quaternary ammonium carboxylate.

84. A metal-free, penetrating waterproofer system as defined in claim 48 wherein said waterproofer composition comprises from about 0.1 to about 20 parts by weight and said solvent comprises from about 80 to about 99.9 percent by weight based upon 100 parts by weight of waterproofer composition and solvent combined.

85. A metal-free, penetrating waterproofer system as defined in claim 84 wherein said waterproofer composition comprises from about 0.2 to about 5 parts by weight and said solvent comprises from about 95 to about 99.8 percent by weight based upon 100 parts by weight of waterproofer composition and solvent combined.

86. A metal-free, penetrating waterproofer wood preservative system as defined in claim 48 wherein said waterproofer composition comprises from about 0.1 to about 15 parts by weight, said quaternary ammonium composition comprises from about 0.1 to about 10 parts by weight, and said solvent comprises from about 99.8 to about 75 parts by weight based upon 100 parts by weight of waterproofer composition, quaternary ammonium composition and solvent combined.

87. A metal-free, penetrating waterproofer wood preservative system as defined in claim 86 wherein said waterproofer composition comprises from about 0.5 to about 6 parts by weight, said quaternary ammonium composition comprises from about 0.5 to about 8.5 parts by weight, and said solvent comprises from about 96 to about 85.5 parts by weight based upon 100 parts by weight of waterproofer composition, quaternary ammonium composition and solvent combined.

88. A method of preparing a metal-free, penetrating waterproofer, wood preservative system comprising:

(A) melting a waterproofing and compatibility enhancing amount of (i) one or more waterproofing composition having the formula

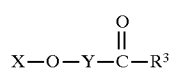

wherein:

X is hydrogen or

Y is selected from the group consisting of Y(l), Y(ii) and Y(iii) wherein Y(l) is

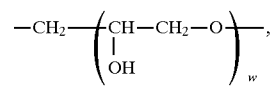

optionally substituted with one or more $C_1$–$C_9$ groups or one or more sulfate groups, interrupted or uninterrupted by one or more oxygen or boron atoms, or any combination thereof, wherein Y(ii) is

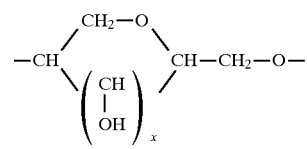

or an enantiomer thereof, optionally substituted with one or more $C_1$–$C_9$ groups or one or more sulfate groups, interrupted or unterrupted by one or more oxygen or boron atoms, or any combination thereof, and wherein Y(iii) is

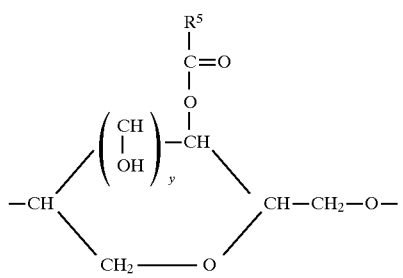

or an enantiomer thereof,
optionally substituted with one or more $C_1$–$C_9$ groups or sulfate groups, interrupted or uninterrupted by one or more oxygen or boron atoms, or any combination thereof wherein the number of carbons in Y ranges from 3–12;

$R^3$, $R^4$, and $R^5$ independently are a saturated or unsaturated $C_9$–$C_{50}$ group, optionally substituted with one or more saturated or unsaturated group, one or more sulfate groups, or a combination thereof, uninterrupted or interrupted with one or more oxygen or boron atoms;

w is an integer from 1 to 10; and x and y are 0, 1, or 2; and (ii) a biocidal effective amount of a quaternary ammonium hydroxide prepared by reacting a $C_8$–$C_{12}$ alkyl or aryl-substituted $C_8$–$C_{12}$ alkyl, dimethyl quaternary ammonium chloride reactant and a metal hydroxide reactant in a solvent comprising a $C_1$–$C_4$ normal alcohol, said metal hydroxide being present in an amount sufficient to yield said alkyl or aryl-substituted $C_8$–$C_{12}$ alkyl, dimethyl quaternary ammonium hydroxide; and (B) adding a solvent to the melt.

* * * * *